(12) United States Patent (10) Patent No.: US 9,120,727 B2
Riedl et al. (45) Date of Patent: Sep. 1, 2015

(54) PROCESS FOR THE PREPARATION OF PLEUROMUTILINS

(75) Inventors: Rosemarie Riedl, Vienna (AT); Werner Heilmayer, Zillingtal (AT); Lee Spence, Vienna (AT)

(73) Assignee: NABRIVA THERAPEUTICS AG, Vienna (AT)

( * ) Notice: Subject to any disclaimer, the term of this patent is extended or adjusted under 35 U.S.C. 154(b) by 0 days.

(21) Appl. No.: 13/699,589

(22) PCT Filed: May 23, 2011

(86) PCT No.: PCT/AT2011/000237
§ 371 (c)(1),
(2), (4) Date: Dec. 12, 2012

(87) PCT Pub. No.: WO2011/146954
PCT Pub. Date: Dec. 1, 2011

(65) Prior Publication Data
US 2013/0079400 A1    Mar. 28, 2013

(30) Foreign Application Priority Data

May 26, 2010    (EP) .................................... 10450092

(51) Int. Cl.
*C07C 205/00* (2006.01)
*C07C 229/00* (2006.01)
*C07C 319/20* (2006.01)
(Continued)

(52) U.S. Cl.
CPC ............. *C07C 319/20* (2013.01); *A61K 31/215* (2013.01); *C07C 53/10* (2013.01); *C07C 57/145* (2013.01); *C07C 59/08* (2013.01); *C07C 319/14* (2013.01); *C07C 323/41* (2013.01); *C07C 323/43* (2013.01); *C07C 323/52* (2013.01); *C07B 2200/07* (2013.01); *C07B 2200/13* (2013.01); *C07C 2101/14* (2013.01); *C07C 2103/82* (2013.01)

(58) Field of Classification Search
None
See application file for complete search history.

(56) References Cited

U.S. PATENT DOCUMENTS

| 2006/0276503 A1 | 12/2006 | Breen et al. |
| 2009/0118366 A1 | 5/2009 | Mang et al. |

FOREIGN PATENT DOCUMENTS

| AT | WO 2008113089 A1 * | 9/2008 |
| WO | WO 2008/113089 | 9/2008 |
| WO | WO 2009-009812 | 1/2009 |

OTHER PUBLICATIONS

Norris (Experimental Organic Chemistry, 1924, McGraw-Hill Book Company Inc., 2nd Edition, 1-4).*
(Continued)

*Primary Examiner* — Dennis Heyer
*Assistant Examiner* — Daniel M Podgorski
(74) *Attorney, Agent, or Firm* — Workman Nydegger

(57) ABSTRACT

Process for the preparation of a compound of formula I

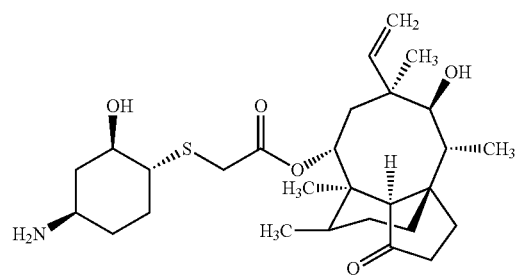

in the form of a single stereoisomer in crystalline form, comprising deprotecting the amine group in a compound of formula IIa

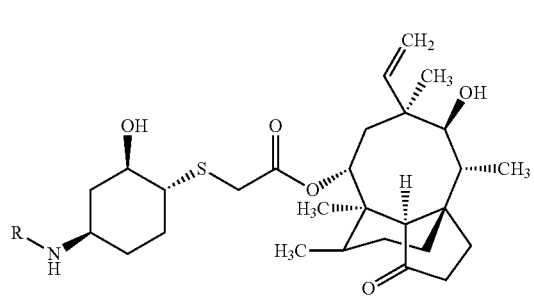

or in a mixture of a compound of formula IIa with a compound of formula IIb

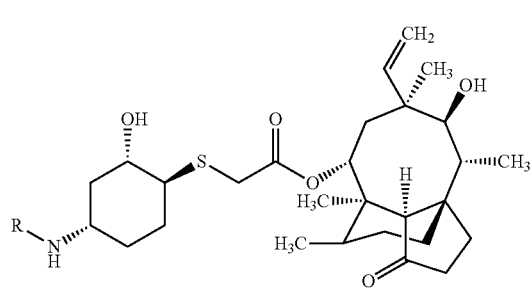

and isolating a compound of formula I from the reaction mixture; compounds and salts of compounds of formula I in crystalline form; pharmaceutical compositions comprising such salts; processes for the preparation of intermediates and intermediates in a process for the preparation of a compound of formula I.

20 Claims, 6 Drawing Sheets

(51) Int. Cl.
- *A61K 31/215* (2006.01)
- *C07C 53/10* (2006.01)
- *C07C 57/145* (2006.01)
- *C07C 59/08* (2006.01)
- *C07C 319/14* (2006.01)
- *C07C 323/41* (2006.01)
- *C07C 323/43* (2006.01)
- *C07C 323/52* (2006.01)
- *A01N 37/00* (2006.01)
- *A61K 31/21* (2006.01)

(56) References Cited

OTHER PUBLICATIONS

Morissette et al. in Drug Delivery Reviews, 56 (2004) 275-300.*

M. Caira, "Crystalline Polymorphism of Organic Compounds", Topics in Current Chemistry, Springer, Berlin, DE, vol. 198, Jan. 1, 1998, pp. 163-208.

Lee et al., "Large-Scale Aspects of Salt Formation: Processing of Intermediates and Final Products", Handbook of Pharmaceutical Salts: Properties, Selection, and Use, Chapter 8, Chapter 12, Jan. 1, 2002, pp. 192, 211-214, 266, 282, 283.

* cited by examiner

PROCESS FOR THE PREPARATION OF PLEUROMUTILINS

The present invention relates to crystalline 14-O-{[(4-amino-2-hydroxy-cyclohexyl)-sulfanyl]-acetyl}-mutilin, new processes for its preparation and crystalline salts thereof.

Pleuromutilin, a compound of formula

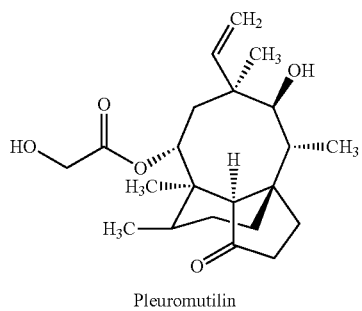 [SMILES: C=C[C@]1(C)C[C@@H](OC(=O)CO)[C@]2(C)C(C)CC[C@]3(CCC(=O)[C@H]32)[C@@H](C)[C@@H]1O]

Pleuromutilin is a naturally occurring antibiotic, e.g. produced by the basidiomycetes *Pleurotus mutilus* and *P. passeckerianus*, see e.g. The Merck Index, 12th edition, item 7694.

A number of further pleuromutilins having the principle ring structure of pleuromutilin and being substituted at the primary hydroxy group have been developed, e.g. as antimicrobials. Due to their pronounced antimicrobial activity, a group of pleuromutilin derivatives, amino-hydroxy-substituted cyclohexylsulfanylacetylmutilins, as disclosed in WO 2008/113089, have been found to be of particular interest. As described in WO2008/11089 14-O-{[(4-Amino-2-hydroxy-cyclohexyl)-sulfanyl]-acetyl}-mutilins are particularly useful compounds because they demonstrate activity against Gram-positive and Gram-negative pathogens e.g. associated with respiratory tract and skin and skin structure infections. For the production of substantially pure isomers/diastereomers of this group of compounds, there is a need for a production process which is convenient for use on an industrial scale and which also avoids the use of costly starting materials, environmentally hazardous reagents and solvents or time consuming and laborious purification steps. The production process described in WO 2008/113089 involves chromatographic purification of the compounds prepared according to individual synthesis steps and the final diastereomers are separated by chiral HPLC chromatography which cannot be used on industrial scale.

Surprisingly, crystalline intermediates have been found which on the one hand have unexpected chemical purification potential which is important for the production processes for pure amino-hydroxy-substituted cyclohexylsulfanylacetylmutilins avoiding chromatographic purification and separation steps.

It has to be pointed out that 14-O-{[(4-amino-2-hydroxy-cyclohexyl)-sulfanyl]-acetyl}-mutilins are potential new drug substances for the human market with regulatory requirements defined in the corresponding ICH guidelines (International Conference on Harmonization of Technical Requirements for Registration of Pharmaceuticals for Human Use). The ICH guideline on impurities in new drug substances (Q3A(R2)) includes the following thresholds:

| Maximium daily dose | Reporting threshold | Identification threshold | Qualification threshold |
|---|---|---|---|
| ≤2 g | 0.05% | 0.10% | 0.15% |
| >2 g | 0.03% | 0.05% | 0.05% |

As can be seen from the ICH thresholds above it is desirable to have all individual unknown impurities below 0.10% area and the structure elucidated impurities below 0.15%, respectively. Processes provided according to the present invention enable to produce APIs (Active Pharmaceutical Ingredients) within the desired specifications and fulfilling ICH requirements.

On the other hand, even more surprisingly, the crystalline intermediates yields to significant chiral enrichment which has a huge benefit in the production of the pure stereoisomers starting from cheaper racemic materials or less chirally pure starting materials. The described processes do not involve any chromatographic purification neither normal nor chiral phase in contrast to the synthetic procedures described in WO2008/113089 wherein is disclosed e.g. in Example 1, Step B that 14-O-{[(4-amino-2-hydroxy-cyclohexyl)-sulfanyl]-acetyl}-mutilins was isolated in the form of diastereomeric mixtures as colorless amorphous foams after normal phase chromatography. The chiral pure diastereomers are described to have been received in WO2008/113089, e.g. in Example 1A after subjecting the mixture to chiral chromatography whereafter the separated pure diastereomers were isolated in the form of colorless amorphous foams.

Chiral chromatography, however is not a technology which can be applied on industrial large scale, and moreover no crystalline salts of 14-O-{[(4-amino-2-hydroxy-cyclohexyl)-sulfanyl]-acetyl}-mutilins were obtained according to WO2008/113089.

In contrast to that, according to the present invention crystalline pharmaceutical acceptable salts of 14-O-{[(4-amino-2-hydroxy-cyclohexyl)-sulfanyl]-acetyl}-mutilins having surprising and superior properties over the amorphic prior art salts disclosed in WO2008/113089 have been found; e.g. surprisingly the chemical stability of the crystalline salts of the present invention is improved over the amorphic salt forms; and also and in addition the crystalline salts of the present invention show a surprising low hygroscopicity.

Processes for the preparation of such crystalline salts wherein the salts may be obtained in a single stereoisomeric form from 14-O-{[(4-amino-2-hydroxy-cyclohexyl)-sulfanyl]-acetyl}-mutilins and processes for the preparation of stereoisomerically pure 14-O-{[(4-amino-2-hydroxy-cyclohexyl)-sulfanyl]-acetyl}-mutilins in crystalline form as a basis for the crystalline salts have also been found.

In one aspect the present invention provides a process for the preparation of a compound of formula I

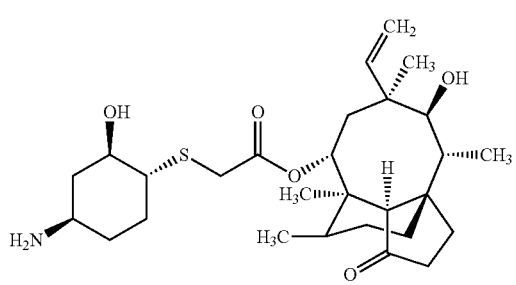

in the form of a single stereoisomer in crystalline form, comprising deprotecting the amine group
either in a compound of formula IIa

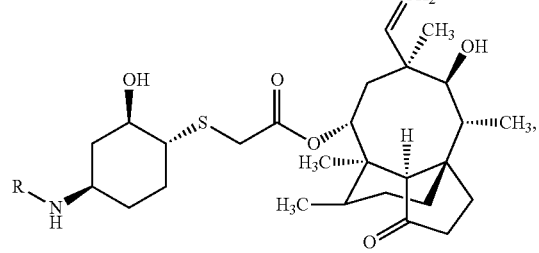

IIa or
in a mixture of a compound of formula IIa with a compound of formula IIb

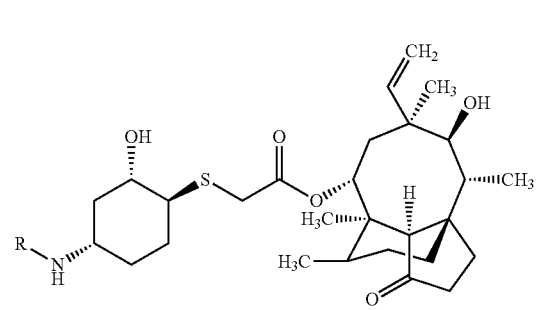

IIb wherein R is an amine protecting group, and isolating a compound of formula I obtained in the form of a single diastereomer in crystalline form either directly from the reaction mixture or via recrystallization in organic solvent.

In another aspect the present invention provides a compound of formula I as defined above in the form of a single stereoisomer in crystalline form.

Compounds of formula IIa are new and also form part of the present invention.

In another aspect the present invention provides a compound of formula IIa.

In a compound of formula I, or IIa, respectively, the carbon atoms of the cyclohexyl ring to which the hydroxy group, the amine group and the sulfanyl-acetyl-mutilin group are attached are all in the R configuration and thus a compound of formula I, or IIa represents an optionally amino protected 14-O-{[(1R,2R,4R)-4-amino-2-hydroxy-cyclohexylsulfanyl]-acetyl}-mutilin. In contrast to that, in a compound of formula Ib

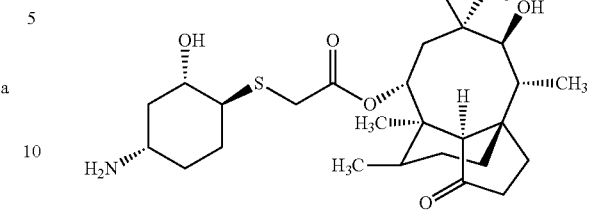

Ib or IIb the carbon atoms of the cyclohexyl ring to which the hydroxy group, the amine group and the sulfanyl-acetyl-mutilin group are attached are all in the S configuration and thus a compound of formula IIb represents an optionally amino protected 14-O-{[(1S,2S,4S)-4-Amino-2-hydroxy-cyclohexylsulfanyl]-acetyl}-mutilin.

An amine protecting group includes protecting groups known to a skilled person and which are removable under acidic, basic, hydrogenating, oxidative or reductive methods, e.g. by hydrogenolysis, treatment with an acid, a base, a hydride, a sulfide. Appropriate amine protecting groups e.g. are described in T. W. Greene, P. G. M. Wuts, *Protective Groups in Organic Synthesis*, Wiley-Interscience, 4$^{th}$ edition, 2007, particularly p. 696-868.

Amine protecting groups which may be conveniently used in a process according to the present invention include for example benzyloxycarbonyl (Cbz), removable e.g. by hydrogenolysis, p-methoxybenzyl carbonyl (Moz or MeOZ), removable e.g. by hydrogenolysis, tert-butyloxycarbonyl (BOC), removable e.g. by treatment with a strong acid, such as HCl, $H_3PO_4$ or $CF_3COOH$, trifluoroacetyl, removable e.g. by treatment with a base, such as NaOH, $K_2CO_3$, $Cs_2CO_3$, 9-fluorenylmethyloxycarbonyl (FMOC), removable e.g. by treatment with a base, such as piperidine, benzyl (Bn), removable e.g. by hydrogenolysis;

p-methoxybenzyl (PMB), removable e.g. by hydrogenolysis;

3,4-dimethoxybenzyl (DMPM), removable e.g. by hydrogenolysis;

p-methoxyphenyl (PMP), removable e.g. by treatment with ammonium cerium(IV) nitrate (CAN), tosyl (Tos), removable e.g. by treatment with concentrated acid, such as HBr, $H_2SO_4$, or by treatment with strong reducing agents, such as sodium in liquid ammonia, sodium naphthalene, groups which form with the amine sulfonamides other than Tos-amides, e.g. including 2-nitrobenzenesulfonamide (nosyl) or o-nitrophenylsulfenyl (Nps), removable e.g. by treatment with samarium iodide, tributyltin hydride, benzylidene, removable e.g. by treatment with trifluoromethanesulfonic acid, trifluoroacetic acid, dimethyl sulfide;

triphenylmethyl (trityl, Tr), dimethoxytrityl (DMT), e.g. removable by treatment with an acid, such as trifluoroacetic acid;

preferably trifluoroacetyl or tert-butyloxycarbonyl (BOC).

In case of trifluoroacetyl a base e.g. an inorganic base, such as NaOH, KOH, $Cs_2CO_3$ and $K_2CO_3$ or an organic base such as ethanolamine may be used to effect deprotection of a compound of formula IIa and IIb to obtain a compound of formula I in the form of a single stereoisomer. In a preferred embodiment an inorganic base, such as NaOH and $K_2CO_3$ is used.

In case of tert-butyloxycarbonyl (BOC) an acid, e.g. an inorganic, such as a mineral acid, or an organic acid may be used to effect deprotection of a compound of formula IIa and IIb to obtain a compound of formula I in the form of a single stereoisomer. In a preferred embodiment an organic acid, such as trifluoroacetic acid (TFA), or a mineral acid, such as ortho phosphoric acid is used.

Alternatively the nitrogen atom to which R is attached form a heterocyclic ring, e.g. the nitrogen atom attached to the cyclohexyl group is part of a phthalimido ring; removable, e.g. by treatment with hydrazine. In this case the hydrogen at the nitrogen is not present (see example 17).

The deprotection of compound of formula IIa leads to the compound of formula I in the form of a single product. In case of deprotection of a mixture of a compound of formula IIa with a compound of formula IIb the obtained products of formulae Ia and Ib are subjected to crystallization/recrystallization and a compound of formula I is obtained out of the mixture.

It has been found that during the amine deprotection reaction the stereochemistry of carbon atoms of the cyclohexyl moiety wherein the thio, hydroxy and amino group, respectively, are attached is retained as in the amine protected compounds of formula IIa and IIb used as a starting material.

Surprisingly it has been found that a compound of formula I may be crystallized after isolation, or even directly in the reaction mixture obtained after deprotection of the amine group. For example a solution of a compound of formula I in a single stereoisomeric form obtained in organic solvent, preferably polar organic solvent, such as $CH_2Cl_2$, is treated with an antisolvent, such as an ether, e.g. diisopropylether (DIPE) or tert-butyl methyl ether (MTBE), preferably DIPE; or a solution of a compound of formula I in a single stereoisomeric form obtained in organic solvent, preferably polar organic solvent, such as $CH_2Cl_2$, is treated after concentration with an organic solvent, preferably an alcohol, such as n-butanol; or an isolated crude material of a compound of formula I in a single stereoisomeric form, is taken up in an organic solvent, such as an ether, e.g. tetrahydrofuran (THF), and optionally treated with an antisolvent, such as an ether, e.g. DIPE or MTBE. A compound of formula I in a single stereoisomeric form, may crystallize and may be isolated in crystalline form.

Crystallization simplifies isolation and handling of the isolated materials and provides excellent opportunities for further purification of the product.

The crystalline compounds obtained according to the present invention may be subjected to further purification, such as recrystallization e.g. out of an organic solvent, preferably an alcohol, such as n-butanol.

(Re)crystallization may be repeated if desired and may result in high recovery yields and excellent purification.

In the following TABLE 1 the surprising high purification potential of the crystalline compound of formula I is indicated.

TABLE 1

| Reaction Stage | HPLC purity (% area) of compound of formula I | Impurity RRT 1.32 (% area) |
|---|---|---|
| Reaction completion after deprotection of IIb | 87.3 | 4.2 |
| After DCM/DIPE crystallization | 95.0 | 2.2 |
| After 1$^{st}$ n-BuOH crystallization | 99.0 | 0.6 |
| After 2$^{nd}$ n-BuOH crystallization 3 | 99.7 | <0.15 |

RRT = relative retention time in the HPLC with respect to I

As clearly can be seen from TABLE 1 above, the purity of a compound of formula I after deprotection of a compound of formula IIa was increased from 87.3% to 95.0% after crystallization and isolation out of DCM ($CH_2Cl_2$)/DIPE. The purity is further increased by n-butanol (re-)crystallizations to a final purity of the isolated compound of formula I of even 99.7%.

TABLE 2 below shows the depletion of selected impurities and overall purification of a recovered compound of formula I from process mother liquors after subjecting to a n-butanol recrystallization:

TABLE 2

| | Initial purity (% area by HPLC) | Purity after n-butanol recrystallization (% area by HPLC) |
|---|---|---|
| Compound I | 96.29 | 99.03 |
| Impurity 1 | 0.61 | 0.14 |
| Impurity 2 | 1.88 | 0.54 |

Crystallization may be enhanced and accelerated by the use of seed crystals. Seed crystals may be obtained by the processes as exemplified herein. The crystallization and recrystallization process of a compound of formula I delivers the desired purity and is highly useful on an industrial scale. The cumbersome and expensive purification by chromatography is circumvented and makes the process industrially applicable.

Even more surprisingly the crystallization of compound I leads to clear diastereomeric enhancement in favor of a compound of formula I when starting from a mixture of a compound of formula I with a compound of formula Ib. After deprotection of a mixture of a compound of formula IIa with a compound of formula IIb and crystallization of the resulting solid in organic solvents or solvent mixtures such as DCM/DIPE results in a significant diastereomeric enhancement. The diastereomeric enhancement is even more pronounced if a recrystallization out of an organic solvent, preferable an alcohol such as n-butanol is performed.

In the following TABLE 3 the chiral enrichment of a compound of formula I in crystalline form is indicated.

TABLE 3

| | Chiral purity determined by chiral HPLC (area %) | |
|---|---|---|
| | 14-O-{[(1R,2R,4R)-4-Amino-2-hydroxy-cyclohexylsulfanyl]-acetyl}-mutilin (compound I) | 14-O-{[(1S,2S,4S)-4-Amino-2-hydroxy-cyclohexylsulfanyl]-acetyl}-mutilin (compound Ib) |
| DCM/DIPE crystallization | 59 | 41 |
| n-butanol crystallization | 93 | 7 |
| Mother liquors | 16 | 84 |

From TABLE 3 it is evident that starting from the diastereomeric mixture of compounds of formulae IIa and IIb in the deprotection step and isolating the resulting products from the reaction mixture via DCM/DIPE crystallization yields to a surprising chiral enhancement of 59:41 in favor of a compound of formula I. Subjecting the resulting enriched product mixture of a compound of formula I and a compound of formula Ib to a n-butanol recrystallization results in a massive and even more surprising enrichment in favor of a compound of formula I in the isolated product (93:7). In contrast to the isolated product of the enriched compound of formula I the n-butanol mother liquor contains almost exclusively a compound of formula Ib (84%).

Optionally recrystallization can be repeated until a desired optical purity is achieved.

The surprising properties of a compound of formula I in crystalline form which are shown in TABLEs 1, 2 and 3 are extremely useful in the preparation of pharmaceutical compounds.

The present invention provides a compound of formula I in single stereoisomeric form in crystalline form.

Surprisingly, two different crystalline forms of a compound of formula I have been isolated and characterized by X-ray powder diffraction.

In another aspect the present invention provides 14-O-{[(1R,2R,4R)-4-amino-2-hydroxy-cyclohexylsulfanyl]-acetyl}-mutilin in crystalline Form 1, e.g. which crystalline Form 1 is characterized by an X-ray powder diffraction pattern with peaks 2-theta at (degrees, ±0.2, inter alia):
10.6, 11.1, 12.0, 14.3, 15.1, 16.1, 21.1; such as:
10.6, 11.1, 12.0, 14.3, 15.1, 16.1, 18.2, 19.2, 20.7, 21.1, 21.3, 21.8, 22.6, 23.5, 24.7, 28.2, 30.2.

In another aspect the present invention provides 14-O-{[(1R,2R,4R)-4-amino-2-hydroxy-cyclohexylsulfanyl]-acetyl}-mutilin in crystalline Form 2, obtained as an 1:1 n-butanol solvate, e.g. which is characterized by an X-ray powder diffraction pattern with peaks 2-theta at (degrees, ±0.2, inter alia):
9.8, 11.1, 13.1, 14.1, 17.6, 19.7, 22.2; such as
9.6, 9.8, 11.1, 13.1, 14.1, 16.0, 17.6, 19.7, 22.2; 22.7, 23.0.

The n-butanol content of 14-O-{[(1R,2R,4R)-4-amino-2-hydroxy-cyclohexylsulfanyl]-acetyl}-mutilin in crystalline Form 2 is between 10 and 18% w/w, typically between 11 and 14% w/w.

A compound of formula I is preferably isolated in the form of a salt, such as a pharmaceutically acceptable salt. Such salts are preferably ammonium salts, namely acid addition salts of the amino group attached to the cyclohexyl ring, and include acetates, lactates, e.g. L-lactates, or maleates, e.g. hydrogenmaleates.

In another aspect the present invention provides a compound of formula I in the form of a single stereoisomer and in the form of a salt, e.g. crystalline salt, wherein a compound of formula I is in the form of a single stereoisomer; the salt preferably is an acetate, lactate, e.g. L-lactate or maleate, e.g. hydrogenmaleate.

Crystalline compounds obtained according to the present invention in a single steroisomeric form of formula I, e.g. in the form of a salt, are useful in a pharmaceutical composition.

In a further aspect the present invention provides a pharmaceutical composition comprising crystalline 14-O-{[((1R,2R,4R)-4-amino-2-hydroxy-cyclohexyl)sulfanyl]acetyl}mutilin, or comprising an, optionally crystalline, acetate, lactate, or hydrogenmaleate of 14-O-{[((1R,2R,4R)-4-amino-2-hydroxy-cyclohexyl)sulfanyl]acetyl}mutilin as an active ingredient in combination with pharmaceutically acceptable carrier or diluent.

Compounds of formula I in free form and in single stereoisomeric form thus obtained may be converted into a salt by addition of an acid to the free base of a compound of formula I. E.g. a compound of formula I may be dissolved or suspended, or is obtained in dissolved or suspended form, in organic solvent, preferably a solvent or solvent mixture, such as an alcohol, e.g. methanol, ethanol; a halogenated hydrocarbon, e.g. dichloromethane; an ether, e.g. tetrahydrofuran, an acetate, such as methyl acetate, ethyl acetate, propyl acetate, isopropyl acetate; a solvent mixture of alcohol with acetate, such as methanol/isopropyl acetate, a solvent mixture of halogenated hydrocarbon with acetate, such as dichloromethane/isopropylacetate, a solvent mixture of ether with acetate, such as tetrahydrofuran/isopropyl acetate, and to the mixture obtained an acid, e.g. an organic acid or an inorganic (mineral) acid, e.g. acetic acid, lactic acid, e.g. L-lactic acid, maleic acid, is added. A compound of formula I, in the form of a salt, e.g. crystalline salt, may be obtained and may be isolated.

It has been found that in the salt formation step the stereochemistry of the carbon atoms of the cyclohexyl ring to which a thio, hydroxy or an amino group is attached, is retained and remains the same as in a compound of formula I in free form.

Isolation of pharmaceutically active compounds as described in WO2008/113089, example I and Ia, respectively, is advantageous; but isolation according to the present invention in crystalline salt form, such as a compound of formula I in crystalline salt form is still much more advantageous. E.g. an improved purity and a surprisingly improved stability of the crystalline salt according to the present invention is highly important and useful for the preparation of pharmaceutical compositions, intended for veterinary and human use. The crystalline salts of a compound of formula I demonstrate improved stability over the corresponding amorphous forms and are isolated with chemical and chiral purity of ≥90%, e.g. even ≥95%.

In the following TABLE 4 comparative stability data of the corresponding crystalline and amorphous salts of compound I are shown.

TABLE 4

| | Area % of 14-O-{[(1R,2R,4R)-4-amino-2-hydroxy-cyclohexylsulfanyl]-acetyl}-mutilin (compound I) by HPLC stored at 60° C. | | | | | |
|---|---|---|---|---|---|---|
| | Acetate (Form B) crystalline | Acetate amorphous | L-Lactate crystalline | L-Lactate amorphous | Hydrogen maleate crystalline | Hydrogen maleate crystalline |
| Initial | 99.5 | 99.3 | 99.4 | 99.5 | 99.7 | 99.6 |
| 28 d | 98.9 | 96.3* | 98.3 | 96.3 | 98.7 | 70.9* |

*sample did not fully dissolve in water after 28 days (28 d) and therefore the suspension was analyzed The solubility of pharmaceutical active compounds is an important property for the in vivo availability e.g. oral bioavailability. For the intravenous application the solubility of the selected form e.g. salt is also very crucial and it is desired of having formulations without sophisticated technologies or exipients.

The solubility of the crystalline acetate, lactate and (hydrogen)maleate salts of the present invention in water and aqueous based vehicles such as 0.9% NaCl solution or in biorelevant media such as FaSSIF (Fasted State Simulated Intestinal Fluid) and FeSSIF (Fed State Simulated Intestinal Fluid) is surprisingly high, which make the crystalline salts of the present invention even more pharmaceutically viable.

The antimicrobial, e.g. antibacterial activity of 14-O-{[(4-amino-2-hydroxy-cyclohexyl)-sulfanyl]-acetyl}-mutilins was outlined in WO2008/113089. For example, the compounds of the present invention e.g. compound of formula I show antimicrobial, e.g. antibacterial, activity against Gram-positive bacteria, such as coagulase positive Staphylococci, e.g. *Staphylococcus aureus* and Streptococci, e.g. *Streptococcus pneumoniae*, e.g. exhibiting MICs<0.4 µg/ml against *Staphylococcus aureus* ATCC49951 and *Streptococcus pneumoniae* ATCC49619. The minimum inhibitory concentration (MIC) was determined in accordance with CLSI recommendations.

In a further aspect the present invention provides crystalline 14-O-{[(1R,2R,4R)-4-amino-2-hydroxy-cyclohexylsulfanyl]-acetyl}-mutilin in the form of an acetate in crystalline Form A, e.g. which is characterized by an X-ray powder diffraction pattern with peaks 2-theta at (degrees, ±0.2, inter alia):
7.0, 7.7, 11.6, 12.1, 12.6, 13.5, 13.7, 15.4, 15.7, 16.9, 17.3, 19.0, 19.9, 21.1, 23.4, 24.2, 24.4; such as
7.0, 7.7, 11.6, 12.1, 12.6, 13.5, 13.7, 14.1, 15.4, 15.7, 16.5, 16.9, 17.3, 19.0, 19.6, 19.9, 20.1, 21.1, 22.2, 22.5, 23.4, 24.2, 24.4, 26.7, 29.1, 29.6, 31.0.

In a further aspect the present invention provides crystalline 14-O-{[(1R,2R,4R)-4-amino-2-hydroxy-cyclohexylsulfanyl]-acetyl}-mutilin in the form of an acetate in crystalline Form B, e.g. which is characterized by an X-ray powder diffraction pattern with peaks 2-theta at (degrees, ±0.2, inter alia):
10.3, 10.7, 12.7, 14.3, 15.5, 16.0, 17.2, 19.5, 20.6, 22.9; such as
9.0, 10.3, 10.7, 12.7, 14.3, 15.5, 16.0, 17.2, 19.5, 20.6, 21.7, 22.3, 22.7, 22.9, 24.4.

In a further aspect the present invention provides crystalline 14-O-{[(1R,2R,4R)-4-amino-2-hydroxy-cyclohexylsulfanyl]-acetyl}-mutilin in the form of an L-lactate in crystalline Form 1, e.g. which is characterized by an X-ray powder diffraction pattern with peaks 2-theta at (degrees, ±0.2, inter alia):
7.0, 11.6, 12.0, 12.5, 13.4, 13.6, 13.9, 15.3, 16.8, 18.8, 19.5, 19.8, 20.9, 23.3, 23.9, 24.2; such as
7.0, 7.6, 11.6, 12.0, 12.5, 13.4, 13.6, 13.9, 15.3, 15.5, 16.8, 17.2, 18.8, 19.5, 19.8, 20.0, 20.9, 22.0, 22.4, 22.7, 23.3, 23.9, 24.2; 25.3, 28.9, 29.4, 30.8

In a further aspect the present invention provides crystalline 14-O-{[(1R,2R,4R)-4-amino-2-hydroxy-cyclohexylsulfanyl]-acetyl}-mutilin in the form of a hydrogenmaleate in crystalline Form 1, e.g. which is characterized by an X-ray powder diffraction pattern with peaks 2-theta at (degrees, ±0.2, inter alia):
7.0, 11.3, 11.7, 12.5, 13.5, 13.8, 15.3, 16.7, 18.3, 19.4, 19.7, 21.1, 22.2, 23.8, 23.9; such as 7.0, 11.3, 11.7, 12.5, 13.3, 13.5, 13.8, 14.1, 15.3, 16.7, 17.2, 18.0, 18.3, 19.4, 19.7, 20.4, 21.1, 21.9, 22.2, 22.8, 23.8, 23.9, 24.9, 27.1, 27.8, 28.7, 29.3, 30.6, 30.8, A compound of formula I in the form of a (crystalline) free base exhibits the same order of pharmaceutical activity, such as antimicrobial activity, than a compound of the present invention in the form of a (crystalline) salt.

A compound of formula IIa in the form of a single stereoisomer or the mixture of a compound of formula IIa with a compound of formula IIb may be prepared as appropriate, e.g. according, e.g. analogously to a method as conventional. Preferably a compound of formula IIa in the form of a single stereoisomer or the mixture of compound of formula IIa with a compound of formula IIb are prepared by coupling an amino-hydroxy-mercapto-cyclohexane compound of formula IIIa, or a mixture of a compound of formula IIIa with a compound of formula IIIb, wherein the amino group is protected with an amino protecting group with an activated 14-O-acetyl-mutilin.

In a further aspect the present invention provides a process according to the present invention, wherein a compound of formula IIa, or a mixture of a compound of formula IIa with a compound of formula IIb is obtained by coupling either a compound of formula IIIa

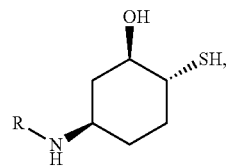

IIIa or
a mixture of a compound of formula IIIa with a compound of formula IIIb

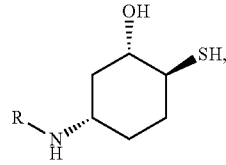

IIIb respectively
wherein R is as defined above,
with an activated 14-O-AKT-acetyl-mutilin of formula

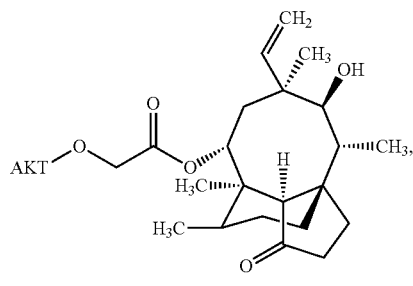

14-O-AKT-acetyl-mutilin wherein AKT is an activating group, optionally mesyl, besyl, tosyl, or —O-AKT is halogen; optionally 14-O-AKT-acetyl-mutilin is a compound of formula

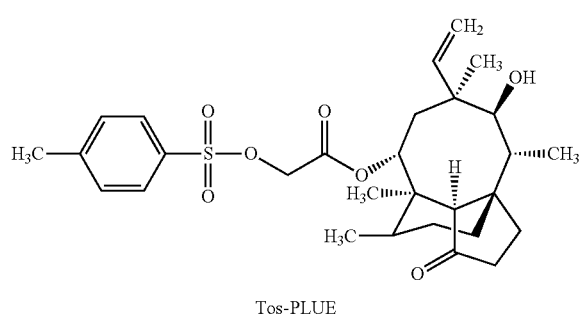

Tos-PLUE and isolating either a compound of formula IIa, or mixture of a compound of formula IIa with a compound of formula IIb obtained from the reaction mixture.

Compounds of formula IIIa wherein R is as defined above are new and also form part of the present invention.

In another aspect the present invention provides a compound of formula IIIa in a single stereoisomeric form.

In a compound of formula IIIa the carbon atoms of the cyclohexyl ring to which the hydroxy group, the amine group and the thio group are attached are all in the R configuration and thus a compound of formula IIIa represents an optionally amino protected (1R,2R,4R)-4-amino-2-hydroxy-1-mercapto-cyclohexane; and in a compound of formula IIIb, respectively, the carbon atoms of the cyclohexyl ring to which the hydroxy group, the amine group and the thio group are attached are all in the S configuration and thus a compound of formula IIIb represents an optionally amino protected (1S,2S,4S)-4-amino-2-hydroxy-1-mercapto-cyclohexane.

The coupling reaction of a compound of formula IIIa or the mixture of a compound of formula IIIa with a compound of formula IIIb, respectively, wherein R is as defined above with an activated 14-O-AKT-acetyl-mutilin, wherein AKT is as defined above, to obtain a compound of formula IIa or a mixture of IIa and IIb, wherein R is as defined above may be performed as appropriate, e.g. according, e.g. analogously to a method as conventional, such as under standard conditions known for those reactions; e.g. in the presence of a base, e.g. a strong inorganic base, like a hydroxide such as NaOH, e.g. in a two phase system, and, if the reaction is performed in a two phase system preferably in the presence of a catalyst, such as a phase transfer catalyst, e.g. benzyl-tri-butylammonium chloride. The coupling reaction may be also performed in a single solvent system, e.g. in organic solvent such as a halogenated hydrocarbon, e.g. chlorobenzene, dichloromethane, an aromatic solvent such as toluene, a nitrile such as acetonitrile or an ether, e.g. tert-butyl-methylether, tetrahydrofuran, in the presence of base, preferably an organic base, such as DBU.

Preferably the coupling reaction is performed in organic solvent, e.g. an apolar solvent, such as an ether, e.g. tert-butyl methyl ether (MTBE) or polar solvent, such as a halogenated hydrocarbon, e.g. dichloromethane; preferably in the presence of an aqueous base solution, such as aqueous NaOH; or in the presence of base in the organic solvent, such as DBU, DBN, preferably in the presence of a phase transfer catalyst in case of using an aqueous base solution, such as benzyl-tri-butylammonium chloride.

It has been found that during the coupling reaction the stereochemistry of the carbon atoms of the cyclohexyl moiety to which the thio, hydroxy and amino group are attached is retained and remains the same as in a compound of formula IIIa and a compound of formula IIIb, respectively, used as a starting material.

A compound of formula IIIa in the form of a single stereoisomer or the mixture of a compound of formula IIIa with a compound of formula IIIb, respectively, may be prepared as appropriate, e.g. according, e.g. analogously to a method as conventional. Preferably a compound of formula IIIa or the mixture of compound of formula IIIa with a compound of formula IIIb, respectively, are prepared by deprotecting the thiol function in an amino-hydroxy-mercapto cyclohexane, wherein the amino group and the thiol group both are protected.

In another aspect the present invention provides a process according to the present invention, wherein a compound of formula IIIa, or a mixture of a compound of formula IIIa with a compound of formula IIIb is obtained by deprotecting the thiol function either in a compound of formula IVa

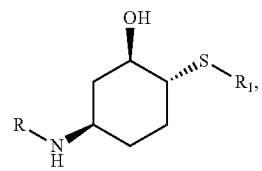

IVa or in a mixture of compound IVa with a compound of formula IVb

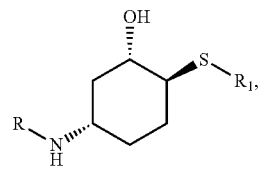

IVb respectively, wherein R is as defined above and $R_1$ is a thiol protecting group, and isolating either a compound of formula IIIa, or a mixture of a compound of formula IIIa with a compound of formula IIIb, respectively, obtained from the reaction mixture.

A thiol protecting group, e.g. in the meaning of $R_1$ in a compound of formulae IVa and IVb according to the present invention, includes e.g.

- $(C_{1-6})$alkyl, wherein alkyl optionally is further substituted, e.g. further substituted by $(C_{6-12})$aryl such as phenyl, such as a trityl; e.g. removable by strong acid or $AgNO_3$ treatment,
- —$(C_{1-6})$alkylcarbonyl, e.g. acetyl, e.g. removable by base, such as sodium methoxide, treatment,
- $(C_{6-12})$arylcarbonyl, such as a benzoyl, e.g. removable by treatment with reduction agent, such as DIBAL, or by treatment with a base, such as hydrazine, preferably —C(=O)—$(C_{6-12})$aryl; more preferably benzoyl.

Appropriate sulfur protecting groups e.g. are described in T. W. Greene, P. G. M. Wuts, *Protective Groups in Organic Synthesis*, Wiley-Interscience, 4th Edition, 2007, particularly p. 647-695.

In a compound of formula IVa the carbon atoms of the cyclohexyl ring to which the hydroxy group, the amine group and the thio group are attached are all in the R configuration and thus a compound of formula IVa represents an amine and thio protected (1R,2R,4R)-4-amino-2-hydroxy-1-mercaptocyclohexane; and in a compound of formula IVb the carbon atoms of the cyclohexyl ring to which the hydroxy group, the amine group and the thio group are attached are all in the S configuration and thus a compound of formula IVb represents an amino and thio protected (1S,2S,4S)-4-amino-2-hydroxy-1-mercapto-cyclohexane.

It has been found that during the thiol deprotection reaction the stereochemistry of the carbon atoms of the cyclohexyl moiety to which the thio, hydroxy and amino group are attached is retained and remains the same as in a compound of formula IVa and in a compound of formula IVb, respectively, used as a starting materials.

Deprotection of the thiol group is carried out as appropriate, e.g. by use of a cleaving agent, e.g. hydrazine hydrate. The deprotection reaction is carried out in an organic solvent, such as a halogenated hydrocarbon, e.g. chlorobenzene, dichloromethane, an aromatic solvent such as toluene, a nitrile such as acetonitrile or an ether, e.g. tert-butyl-methyl-ether, tetrahydrofuran. In order to minimize disulfide formation, deprotection is optionally performed in the presence of an antioxidant or reducing agent, e.g. dithiothreitol (DTT).

A compound of formula IVa or a mixture of compound of formula IVa with a compound of formula IVb, respectively may be obtained as appropriate, e.g. analogously to a method as conventional or as described herein, e.g. in the example part.

In another aspect the present invention provides
a process for the production of a compound of formula I in the form of a single stereoisomer, comprising using a compound of formula IIa in the form of a single stereoisomer, or a mixture of compound of formula IIa with a compound of formula IIb, respectively, and/or comprising using a compound of formula IIIa in the form of a single stereoisomer, or a mixture of a compound of formula IIIa with a compound of formula IIIb, respectively, and/or using a compound of formula IVa in the form of a single stereoisomer, or a mixture of a compound of formula IVa with a compound of formula IVb, respectively, as an intermediate, and
a compound of formula IIa in the form of a single stereoisomer, and/or a compound of formula IIIa in the form of a single stereoisomer, and/or a compound of formula IVa in the form of a single stereoisomer for use as an intermediate in a process for the production of a compound of formula I in the form of a single stereoisomer.

In a further aspect the present invention provides a process for the production of a compound of formula I in the form of a single stereoisomer, comprising coupling a compound of formula IIIa in the form of a single stereoisomer, or a mixture of a compound of formula IIIa with a compound of formula IIIb, respectively, wherein R is as defined above, with an activated 14-O-AKT-acetyl-mutilin, wherein AKT is an activating group, such as a mesyl, besyl or tosyl group, or —O-AKT is halogen, preferably AKT is a tosyl group, e.g. a compound of formula Tos-PLEU, to obtain a compound of formula IIa or a mixture of compound of formula IIa with a compound of formula IIb, respectively, wherein R is as defined above,
optionally isolating a compound of formula IIa in the form of a single stereoisomer, or a mixture of a compound of formula IIa with a compound of formula IIb, respectively,
wherein R is as defined above, obtained from the reaction mixture,
deprotecting the amine function in a compound of formula IIa in the form of a single stereoisomer, a mixture of a compound of formula IIa with a compound of formula IIb, respectively, wherein R is as defined above, obtained, and
isolating a compound of formula I in the form of a single stereoisomer, optionally in the form of a salt; from the reaction mixture optionally via recrystallization, and, if desired, converting a compound of formula I in the form of a single stereoisomer obtained in free form into a compound of formula I in salt form in the form of a single stereoisomer, or vice versa;
wherein optionally a compound of formula IIIa in the form of a single stereoisomer or a mixture of a compound of formula IIIa with a compound of formula IIIb, respectively, wherein R is as defined above, is obtained by deprotection of the thiol function in a compound of formula IVa in the form of a single stereoisomer, or in a mixture of a compound of formula IVa with a compound of formula IVb, wherein R and $R_1$ are as defined above.

As an amine protecting group in a compound of formula IIa, IIb, IIIa, IIIb, IVa or IVb conventional amino protecting groups may be used, preferably a trifluoroacetyl or tert-butoxycarbonyl group. If appropriate the amine protecting group R in a compound of formula IIa, IIb, IIIa, IIIb, IVa or IVb may be changed, in a way that the carbon atom of the cyclohexyl ring to which the amine group is attached does not change its configuration, i.e. does not change stereochemistry, e.g. via deprotection of the amine group, followed by protection with a different amine protecting group.

The processes of the present invention enables the isolation of compounds of formula I in the form of a single stereoisomer in crystalline form. On the one hand the process controls, when starting from chiral pure starting materials, stereochemistry and yields products in the form of single stereoisomers whereby no sophisticated methods like chromatography, e.g. normal phase or chiral phase, e.g. chiral HPLC, are necessary to separate the mixtures of diastereomers and regioisomers, e.g. as described in WO 2008/113089 which is a big advantage with respect to an industrially applicable process. The discovery of the crystalline compound of formula I is the key invention and enables perfect control of the chemical purity. In conjunction with the observed desirable yields of the crystalline forms of a compound of formula I, the processes of the present invention are extremely viable for the production of a pharmaceutical where a decent/good yield is needed from an economic point of view and the control of the purity is essential for the final quality of the active pharmaceutical ingredient (API).

On the other hand the processes according to the present invention control even more surprisingly the chiral purity of a compound of formula I again via surprising properties of crystalline compound I. The surprising properties of crystalline compound I enable to start from much less expensive diastereomeric mixtures. The chiral purity is controlled at the crystalline compound I whereby compound I is isolated in the form of a crystalline solid and the unwanted diastereomer is depleted to the mother liquor.

By no means the existence of a compound of formula I in crystalline form is described in WO 2008/113089. In example 1 Step B of WO 2008/113089 the mixture of 14-O-{[(1R,2R,4R)-4-amino-2-hydroxy-cyclohexylsulfanyl]-acetyl}-mutilin (compound I of the present invention) and 14-O-{[(1S,2S,4S)-4-amino-2-hydroxy-cyclohexylsulfanyl]-acetyl}-mutilin are isolated as amorphous foams. Example 1A in WO 2008/113089 describes the separation of the diastereomers via chiral chromatography and the separated 14-O-{[(1R,2R,4R)-4-amino-2-hydroxy-cyclohexylsulfanyl]-acetyl}-mutilin (compound I of the present invention) and 14-O-{[(1S,2S,4S)-4-amino-2-hydroxy-cyclohexylsulfanyl]-acetyl}-mutilin (compound Ib of the present invention) are again isolated as amorphous foams.

The surprising properties of the crystalline compounds I controlling the chemical and chiral purity of compound I are extremely valuable for the production of a pharmaceutical active compound to be administered to humans or animals.

The present invention further relates to a novel crystalline forms of 14-O-{[(1R,2R,4R)-4-amino-2-hydroxy-cyclohexylsulfanyl]-acetyl}-mutilin in the form of an acetate, L-lactate or hydrogenmaleate. 14-O-{[(1R,2R,4R)-4-Amino-2-hydroxy-cyclohexylsulfanyl]-acetyl}-mutilin may be converted to the crystalline salt forms using a crystallization process in organic medium with the salt forming agent. The process for the production of the novel crystalline salts may be enhanced and accelerated by the use of seed crystals. Seed crystals may be obtained by the exemplified processes.

It has been found that the crystalline salts of the present invention retain the stereochemistry of a compound of formula I in free form in the form of a single stereoisomer. The crystalline salts according to the present invention have clear unexpected advantages i.e. enhanced stability over the corresponding amorphous salt forms, as e.g. is evident from TABLE 4.

Moreover and rather surprisingly the hygroscopicity of the crystalline salts of the present invention, preferebly the L-lactate and the acetate salt in crystalline Form B is small between relevant humidity levels, i.e. between 0-80% relative humidity with a water uptake of below 2% making the salts in conjunction with the excellent chemical stability pharmaceutically viable.

The crystalline salts of the present invention are of desired and consistent chemical and chiral purity, have better stability compared to the amorphous lyophilized forms, being advantageous in the storage and for the preparation of pharmaceutical compositions. No crystalline salt form of a compound of formula I has been described before, e.g. in WO 2008/113089.

Overall, the crystalline salt forms of a compound of formula I have excellent purities and the observed stability was not only superior to the amorphous salt forms but have proofen to be absolutely pharmaceutically viable within the range of normal storage conditions.

"In the form of a single stereoisomer" as used herein designates a form wherein the compound shows a diastereomeric or enantiomeric excess of ≥90% of the indicated stereochemistry.

Particularly preferred compounds of the present invention include the compounds of Examples 1 to 17, e.g. a compound selected from the group consisting of
tert-Butyl[(1R,3R,4R)-3-hydroxy-4-mercapto-cyclohexyl]-carbamate,
14-O-{[(1R,2R,4R)-4-tert-Butoxycarbonylamino-2-hydroxy-cyclohexyl-sulfanyl]-acetyl}-mutilin,
14-O-{[(1R,2R,4R)-4-Amino-2-hydroxy-cyclohexylsulfanyl]-acetyl}-mutilin, crystalline Form 1,
14-O-{[(1R,2R,4R)-4-Amino-2-hydroxy-cyclohexylsulfanyl]-acetyl}-mutilin, crystalline Form 2,
2,2,2-Trifluoro-N-[(1R,3R,4R)-3-hydroxy-4-mercapto-cyclohexyl]-acetamide,
14-O-{[(1R,2R,4R)-4-[(2,2,2-Trifluoro-acetyl)-amino]-2-hydroxy-cyclohexyl-sulfanyl]-acetyl}-mutilin,
14-O-{[(1R,2R,4R)-4-Amino-2-hydroxy-cyclohexyl-sulfanyl]-acetyl}-mutilin acetate, crystalline Form A,
14-O-{[(1R,2R,4R)-4-Amino-2-hydroxy-cyclohexyl-sulfanyl]-acetyl}-mutilin acetate, crystalline Form B,
14-O-{[(1R,2R,4R)-4-Amino-2-hydroxy-cyclohexylsulfanyl]-acetyl}-mutilin L-lactate, crystalline Form 1,
14-O-{[(1R,2R,4R)-4-Amino-2-hydroxy-cyclohexylsulfanyl]-acetyl}-mutilin hydrogenmaleate, in crystalline Form 1,
14-O-{[(1R,2R,4R)-4-ethoxycarbonylamino-2-hydroxy-cyclohexyl-sulfanyl]-acetyl}-mutilin, and
14-O-{[(1R,2R,4R)-2-hydroxy-4-(phtalimido-N-yl)-cyclohexyl-sulfanyl]-acetyl}-mutilin.

Figure 1:
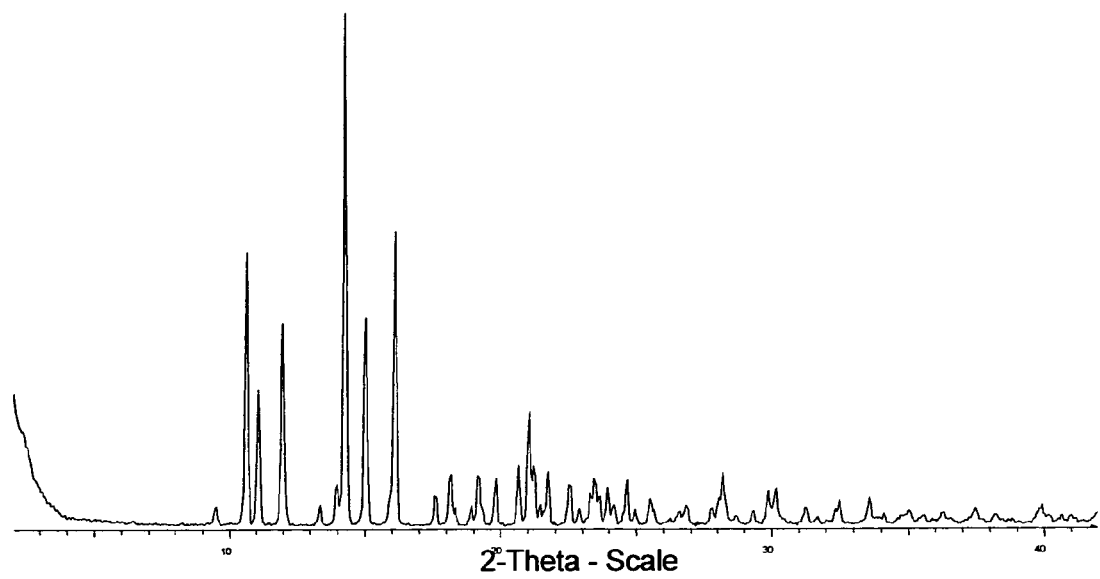
In FIG. 1 the Powder Diffractogram of 14-O-{[(1R,2R,4R)-4-amino-2-hydroxy-cyclohexylsulfanyl]-acetyl}-mutilin, Form 1 is indicated.
Figure 2:
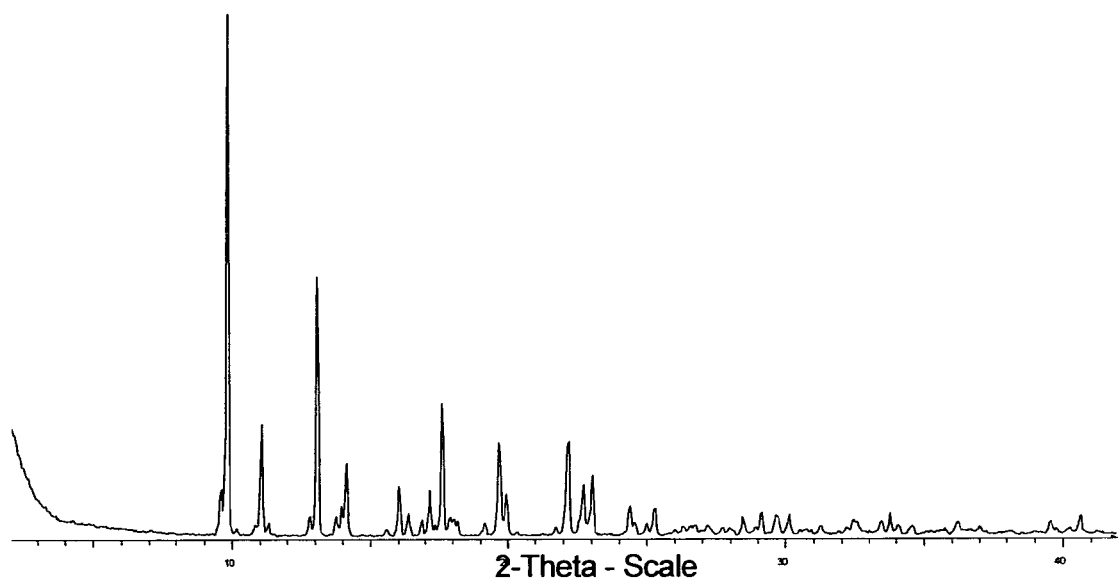
FIG. 2 shows the Powder diffractogram of 14-O-{[(1R,2R,4R)-4-amino-2-hydroxy-cyclohexylsulfanyl]-acetyl}-mutilin, Form 2.
Figure 3:
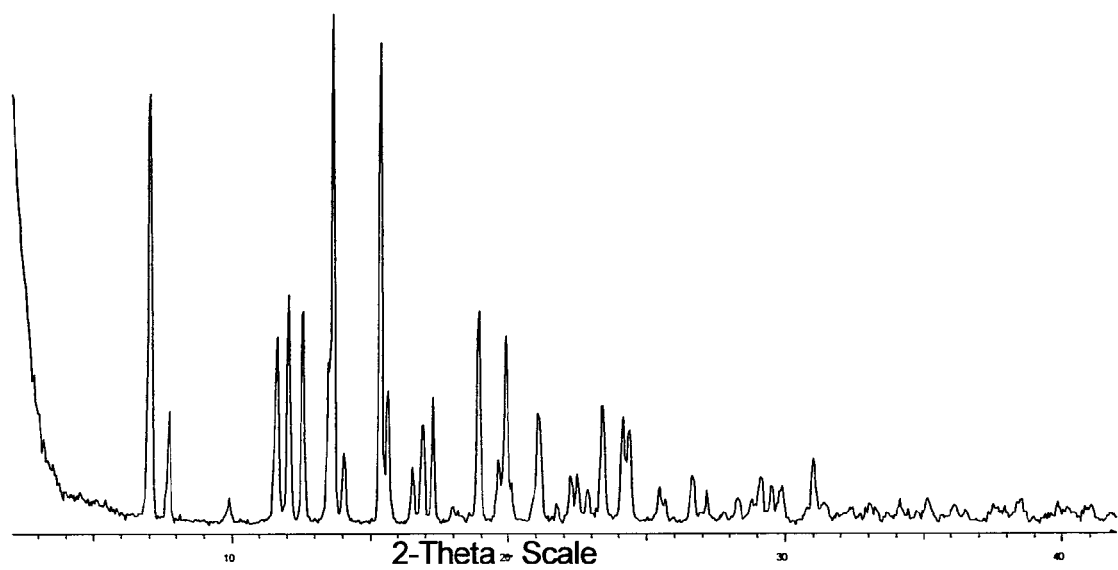
FIG. 3 shows the Powder diffractogram of 14-O-{[(1R,2R,4R)-4-amino-2-hydroxy-cyclohexylsulfanyl]-acetyl}-mutilin in the form of an acetate, Form A.
Figure 4:
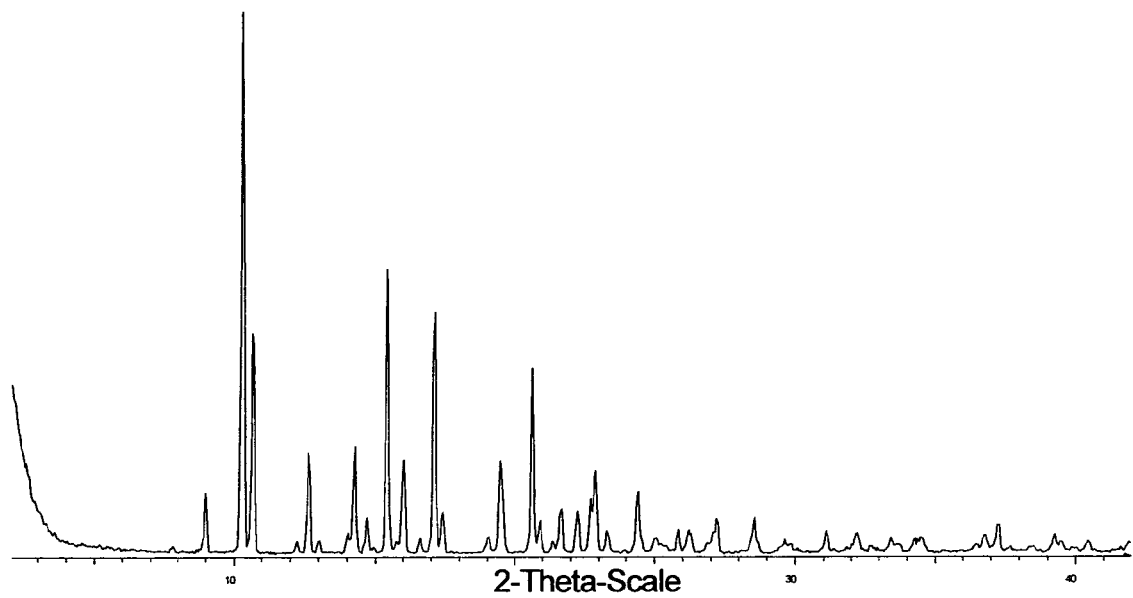
FIG. 4 shows the Powder diffractogram of 14-O-{[(1R,2R,4R)-4-amino-2-hydroxy-cyclohexylsulfanyl]-acetyl}-mutilin in the form of an acetate, Form B.
Figure 5:
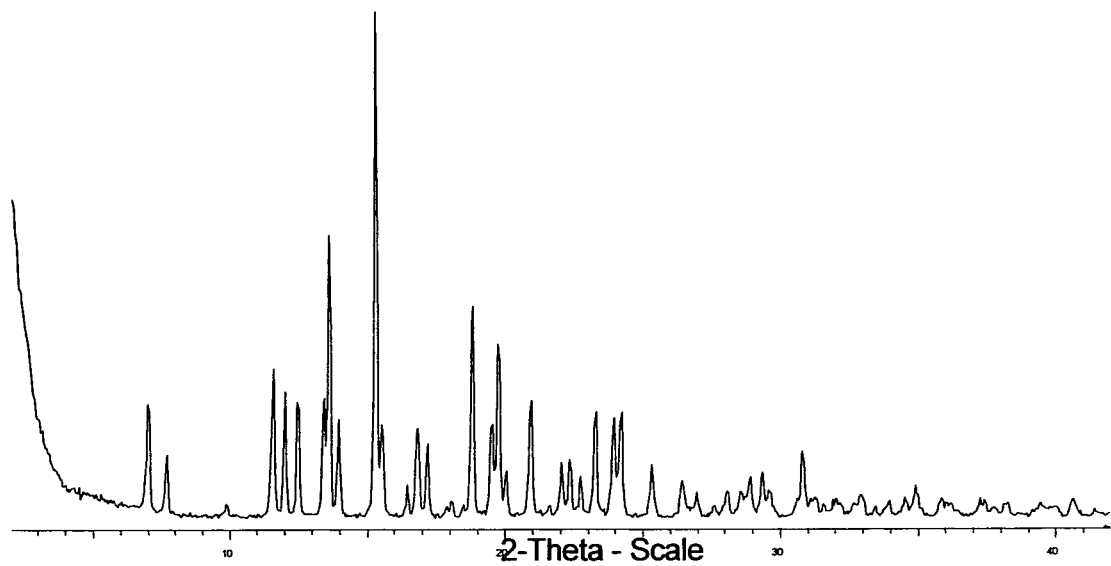
FIG. 5 shows the Powder diffractogram of 14-O-{[(1R,2R,4R)-4-amino-2-hydroxy-cyclohexylsulfanyl]-acetyl}-mutilin in the form of an L-lactate, Form 1.
Figure 6:
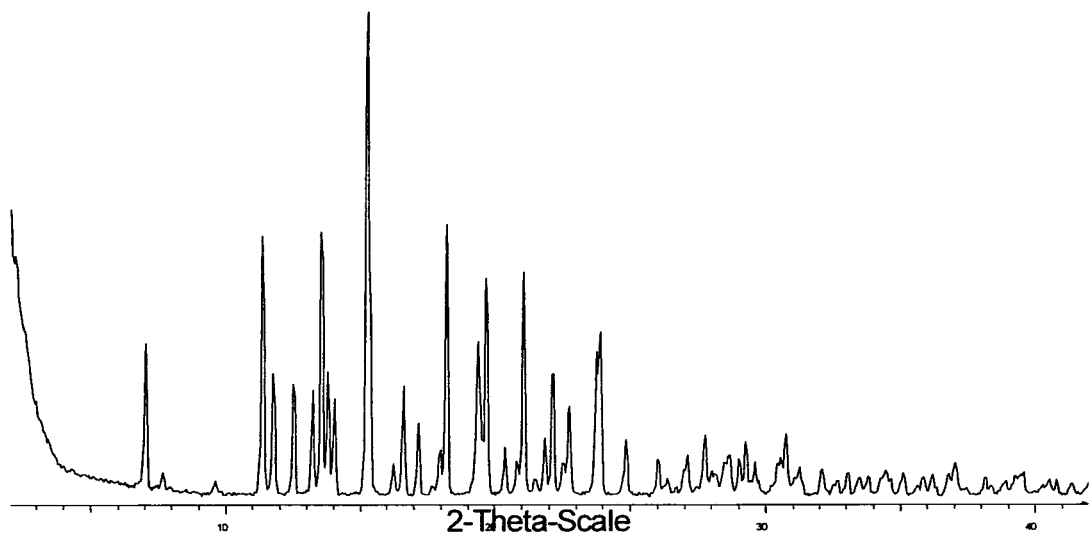
FIG. 6 shows the Powder diffractogram of 14-O-{[(1R,2R,4R)-4-amino-2-hydroxy-cyclohexylsulfanyl]-acetyl}-mutilin in the form of a hydrogenmaleate, Form 1.

The process for the synthesis of a compound of formula I starting from the chiral precursors IIa, IIIa and IVa is summarized in REACTION SCHEME 1 below:

REACTION SCHEME 1

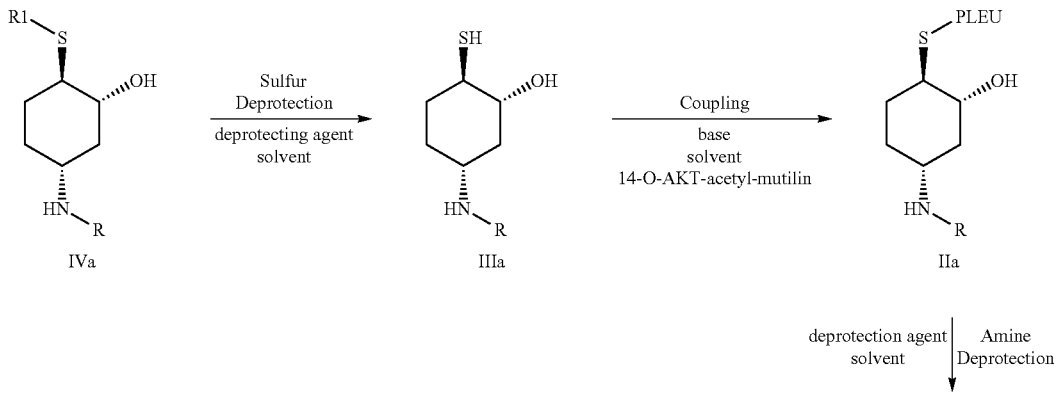

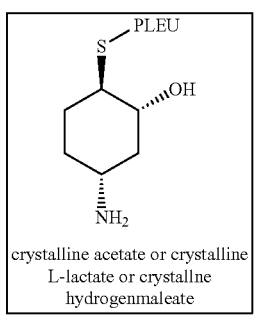
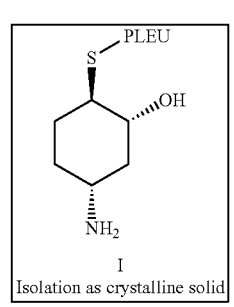
In REACTION SCHEME 1 R represents an amino protecting group and $R_1$ represents a sulfur protecting group and are as defined above.
The process for the synthesis of a compound of formula I starting from the mixtures of IIa with IIb, IIIa with IIIb and IVa with IVb is summarized in REACTION SCHEME 2 below:
REACTION SCHEME 2
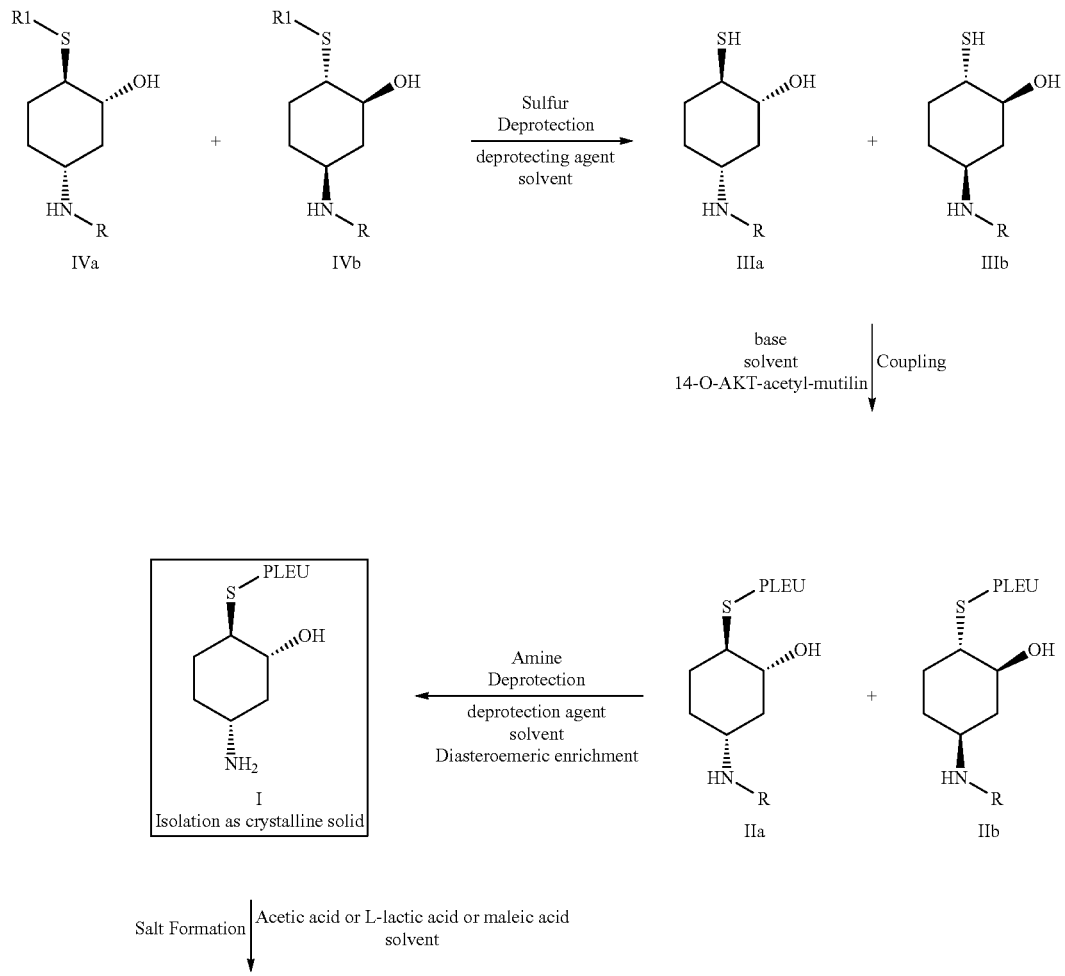

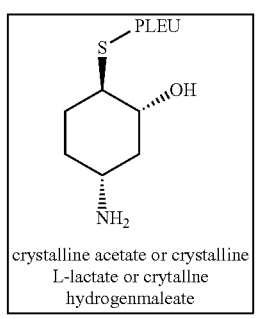

crystalline acetate or crystalline L-lactate or crytallne hydrogenmaleate

In REACTION SCHEME 2 R represents an amino protecting group and $R_1$ represents a sulfur protecting group (R and $R_1$ as defined above).

Herein, including the examples and including REACTION SCHEMES 1, 2, 3, 4, 5 and 6 the following abbreviations are used:
° C. degrees Celsius
$^1$H NMR proton nuclear magnetic resonance spectroscopy
$^{13}$C NMR carbon nuclear magnetic resonance spectroscopy
$[\alpha]_D$ specific optical rotation angle at 589 nm
BnBu$_3$NCl benzyltributylammonium chloride
BOC tert-butoxycarbonyl
d days
DCM CH$_2$Cl$_2$
DIBAL diisobutylaluminium hydride
DBN 1,5-diazabicyclo[4.3.0]non-5-ene
DBU 1,8-diazabicyclo[5.4.0]undec-7-ene
DIPE diisopropylether
DMF N,N-dimethylformamide
DMSO dimethylsulfoxide
DMTF dimethylthioformamide
DPPA diphenylphosphoryl azide
DTT 1,4-dithio-DL-threitol
ESI electrospray ionization
EtOAc ethyl acetate
GF glass fibre
h hours
heptane n-heptane
HPLC High Performance Liquid Chromatography
KF Karl Fischer
M molarity
mCPBA metachloroperoxybenzoic acid
MTBE methyl tert-butyl ether
min minutes
MS mass spectrometry
m/z mass/charge ratio
t-BuOH tert-butylalcohol
Bu$_4$NCl tetra-n-butylammonium chloride
PhCOSH thiobenzoic acid
rt room temperature
TLC thin layer chromatography
TEA, Et$_3$N triethylamine
TFA trifluoroacetic acid
THF tetrahydrofuran
Wt weight
w/w weight/weight
XRPD powder X-ray diffraction A "strip weight assay" as indicated in the examples is defined as follows: The content of an aliquot of a batch or of the whole batch is determined by removing the solvent and determining the content by HPLC or NMR using an internal or external standard and/or subtracting known impurities from the compound. In case of taking an aliquot a back extrapolation to the total mass/volume is performed.

A "line rinse" as indicated in the examples is a system rinse using an appropriate solvent to minimize losses of product and input materials.

Tos-PLEU is a compound of formula

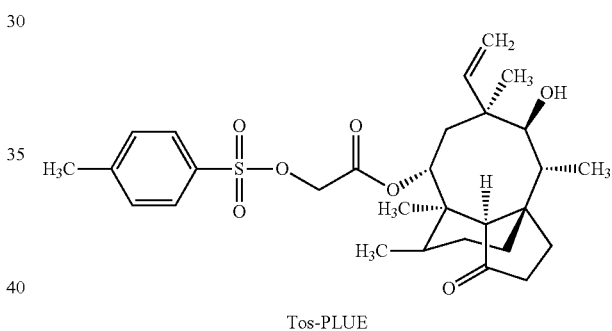

Tos-PLUE

PLEU is a residue of formula

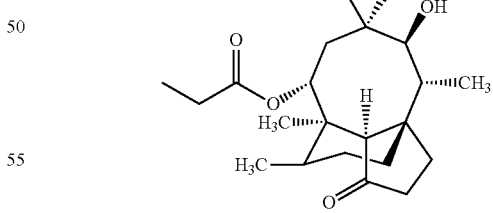

Any compound provided by the present invention is also designated herein as "a compound(s) of (according to) the present invention" and any process provided by the present invention is designated herein as "a process(es) of (according to) the present invention".

Any compound of the present invention may be obtained as appropriate, e.g. analogously to a method as conventional or as described herein.

1H), 2.37 (d, J=3.8 Hz, 1H), 2.00-1.89 (m, 1H), 1.87-1.82 (m, 1H), 1.73-1.67 (m, 1H), 1.47-1.04 (m, 12H)

Example 1 tert-Butyl[(1R,3R,4R)-3-hydroxy-4-mercapto-cyclohexyl]-carbamate

Example 2

22-O-Tosylpleuromutilin

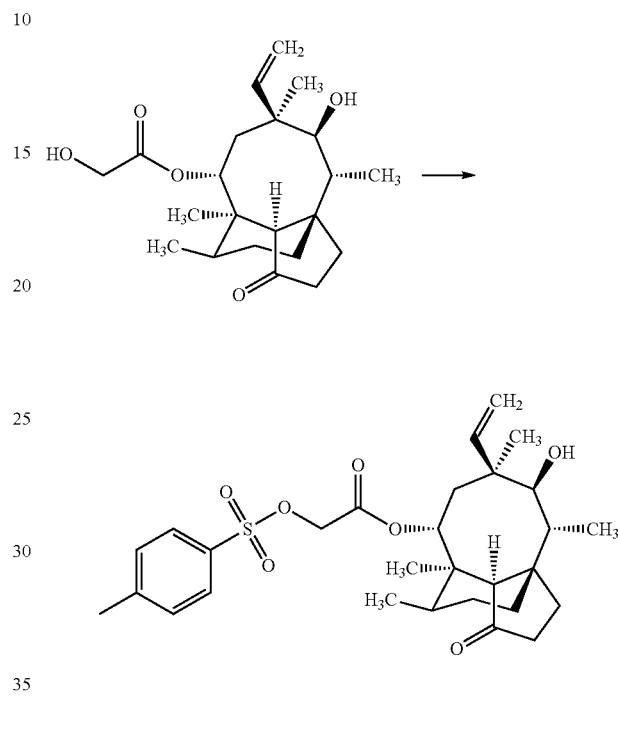

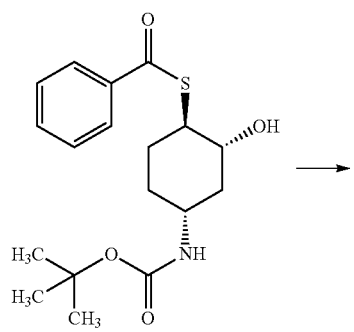

3.94 Kg of {(1R,2R,4R)-4-[tert-Butoxycarbonyl)-amino]-2-hydroxy-cyclohexyl}-benzene-carbothioate and 37 L of $CH_2Cl_2$ were charged to a vessel and the mixture obtained was stirred at 15-25° C. 0.39 Kg of 1,4-dithio-DL-threitol (10% wt) was added to the mixture and rinsed through with 2 L of $CH_2Cl_2$. To the mixture obtained 0.84 Kg of hydrazine monohydrate was added. The mixture obtained was stirred at 18 to 22° C. for 3 h and the reaction was followed by HPLC. Upon completion of the reaction, 39 L of 1 M phosphoric acid solution was added and the mixture obtained was stirred for a further 15-30 min. Two phases formed were separated and the organic phase obtained was washed with 39 L of 1 M phosphoric acid solution followed by 39 L 1% aqueous NaCl solution. The organic layer obtained was concentrated in vacuo at <40° C., to the concentration residue 20 L of $CH_2Cl_2$ was added and the mixture obtained again was concentrated. To the concentration residue obtained a further 8 L of $CH_2Cl_2$ was added and the mixture obtained was concentrated to dryness.

2.89 Kg of tert-Butyl[(1R,3R,4R)-3-hydroxy-4-mercapto-cyclohexyl]-carbamate in the form of a white solid was obtained.

$^1$H NMR (200 MHz, DMSO-$d_6$, ppm) δ 6.79 (d, J=7.8 Hz, 1H), 4.99 (d, J=5.8 Hz, 1H), 3.34-3.24 (m, 1H), 3.14-3.04 (m, 22-O-Tosylpleuromutilin is a known compound from literature. However a preparation procedure is outlined below.

A solution of 13.0 kg of pleuromutilin and 6.57 kg of 4-toluenesulfonyl chloride in 42.1 L of $CH_2Cl_2$ at 10 to 15° C. was treated with 9.1 L of 5.7 M aqueous NaOH over 20 min, maintaining a temperature <25° C. The resulting off-white suspension was heated to reflux for 20 h and the reaction was followed until completion determined by HPLC. Upon reaction completion the mixture obtained was cooled to 20 to 30° C., diluted with 52 L of $CH_2Cl_2$, stirred at 15 to 25° C. for 10 min, and the layers obtained were separated. The organic phase obtained was washed several times with 52 L of water until a pH of the aqueous layer was adjusted to <9. The organic layer obtained was concentrated to 4 volumes and azeotropically dried twice with 52 L of $CH_2Cl_2$. To the solution obtained 52 L of heptane were added dropwise and the solution obtained was concentrated at <40° C. to approximately 4 volumes. To the concentrate obtained 52 L of heptane was added and the resulting suspension was stirred at 20 to 25° C. for 2 to 2.5 h, filtered, the filter cake obtained was washed with 39 L of heptane and pulled dry on the filter.

The solid was dried under vacuum at <40° C. for at least 12 h.

16.9 kg of 22-O-tosylpleuromutilin in the form of a white solid was obtained.

$^1$H NMR (200 MHz, DMSO-$d_6$, ppm, inter alia) δ 7.81 (d, 2H), 7.47 (d, 2H), 6.14-6.0 (m, 1H), 5.54 (d, J=7.8 Hz, 1H), 5.08-4.99 (m, 2H), 4.70 (AB, J=16.2 Hz, 2H), 3.41 (d, J=5.2 Hz, 1H), 2.41 (s, 4H), 1.04 (s, 3H), 0.81 (d, 3H), 0.51 (d, 3H)

Example 3

14-O-{[(1R,2R,4R)-4-tert-Butoxycarbonylamino-2-hydroxy-cyclohexyl-sulfanyl]-acetyl}-mutilin

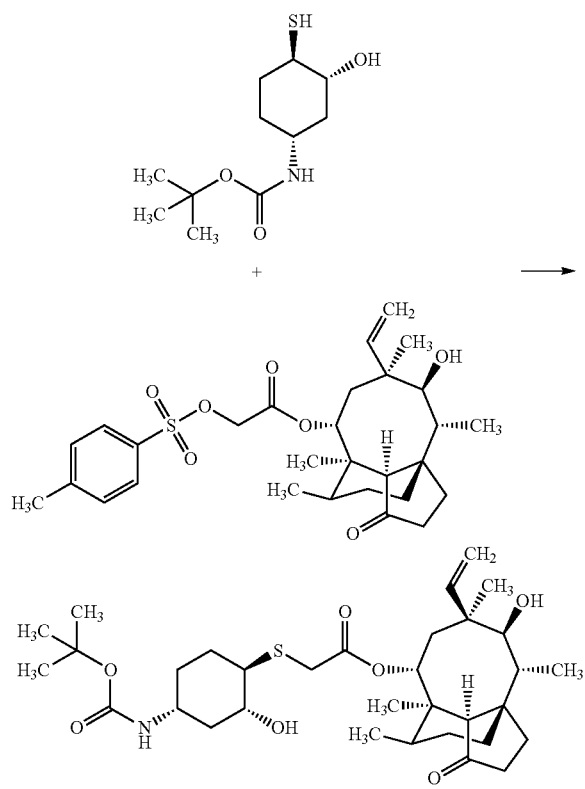

4.75 Kg of Pleuromutilin tosylate (Tos-PLEU) and 44.4 L of MTBE were charged into a vessel and to the mixture obtained 0.31 Kg of benzyl-tri-n-butylammonium chloride was added and rinsed through with 2.4 L of MTBE. To the mixture obtained 20 L of 1M aqueous NaOH solution and 2.84 Kg of tert-Butyl[(1R,3R,4R)-3-hydroxy-4-mercapto-cyclohexyl]-carbamate were added and the mixture obtained was stirred at 17 to 23° C. for 3 h. Upon completion of the reaction (determined by HPLC) two layers formed were separated and the lower aqueous layer was removed. The organic phase obtained was washed with 19 L of 1M aqueous NaOH solution, twice with 20 L of 0.1 M phosphoric acid, 20 L of 10% aqueous NaHCO$_3$ solution and twice with 20 L of water. The organic liquors obtained were concentrated, the concentrate obtained was taken up in 7.46 Kg of 2-propanol, the mixture obtained was concentrated again and dried in vacuo at <40° C. 6.66 Kg of 14-O-{[(1R,2R,4R)-4-tert-Butoxycarbonylamino-2-hydroxy-cyclohexyl-sulfanyl]-acetyl}-mutilin in the form of a white foam was obtained.

$^1$H NMR (200 MHz, DMSO-d$_6$, ppm, inter alia) δ 6.78 (d, J=7.8 Hz, 1H), 6.22-6.08 (m, 1H), 5.55 (d, J=7.8 Hz, 1H), 5.13-5.02 (m, 2H), 4.95 (d, J=5 Hz, 1H), 4.52 (d, J=6 Hz, 1H), 3.36 (AB, J=15 Hz, 2H), 2.40 (s, broad, 1H), 2.15-2.0 (m, 3H), 1.9-1.8 (m, 1H), 1.35 (s, 9H), 0.81 (d, J=7 Hz, 3H), 0.62 (d, J=6.6 Hz, 3H)

MS (ESI, g/mol): m/z 653 [M+2Na]$^+$

Example 4

14-O-{[(1R,2R,4R)-4-Amino-2-hydroxy-cyclohexyl-sulfanyl]-acetyl}-mutilin, crystalline Form 2

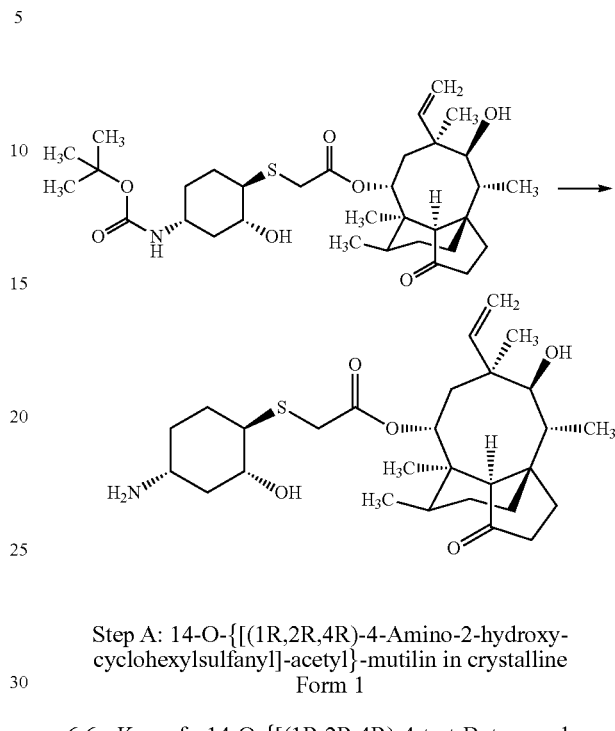

Step A: 14-O-{[(1R,2R,4R)-4-Amino-2-hydroxy-cyclohexylsulfanyl]-acetyl}-mutilin in crystalline Form 1

6.6 Kg of 14-O-{[(1R,2R,4R)-4-tert-Butoxycarbonylamino-2-hydroxy-cyclohexyl-sulfanyl]-acetyl}-mutilin and 13.2 L of isopropanol were charged into a vessel and stirred at 20 to 25° C. 11.20 kg of 85% phosphoric acid was added and the mixture obtained was heated to approximately 50° C. for at least 16 h. The mixture obtained was analyzed for reaction completion by HPLC. Upon completion of the reaction the mixture was cooled to 20 to 25° C. and 52 L of CH$_2$Cl$_2$ was added. The mixture obtained was cooled to 0 to 5° C. and 51 L of 30% aqueous K$_2$CO$_3$ solution was added over 1 h at <25° C. The mixture obtained was warmed to rt, stirred for 30 min and the pH of the aqueous layer was determined. To the mixture obtained a further 15 L of 30% aqueous K$_2$CO$_3$ solution was added at <25° C., the mixture obtained was stirred at 15° C. to 25° C. for 30 min and the two phases obtained were separated. The aqueous phase obtained was extracted with 51 L of CH$_2$Cl$_2$ and the combined organic phases were washed with 51 L of purified water. The mixture obtained was concentrated to a volume of 25 L, 33.6 Kg of CH$_2$Cl$_2$ was added and the mixture obtained was concentrated to 25 L. To the concentrate obtained 33.6 Kg of CH$_2$Cl$_2$ was added and the mixture obtained was concentrated to 10 L. The concentration residue obtained was cooled to 18 to 22° C. and 50 L of di-isopropyl ether was added over a period of 1 h. The slurry obtained was stirred at 15 to 25° C. for a minimum of 2 h, filtered and the solid obtained was washed with 10 L of di-isopropyl ether and was dried.

3.79 Kg of 14-O-{[(1R,2R,4R)-4-Amino-2-hydroxy-cyclohexylsulfanyl]-acetyl}-mutilin in crystalline Form 1 was obtained.

Step B: 14-O-{[(1R,2R,4R)-4-amino-2-hydroxy-cyclohexylsulfanyl]-acetyl}-mutilin, in crystalline Form 2

For further purification 14-O-{[(1R,2R,4R)-4-Amino-2-hydroxy-cyclohexylsulfanyl]-acetyl}-mutilin from Step A and 18.75 L of n-butanol were heated to 88 to 92° C. until complete dissolution and stirred for 30 to 60 min. The mixture obtained was allowed to cool to 40 to 45° C. over at least 2 h and further stirred at this temperature for 2 h. The mixture obtained was filtered and the precipitate obtained was washed with 3.75 L of n-butanol followed by 3.75 L of MTBE. That purification procedure was repeated and the resultant product was dried in vacuo at <40° C.

3.27 Kg of crystalline 14-O-{[(1R,2R,4R)-4-amino-2-hydroxy-cyclohexylsulfanyl]-acetyl}-mutilin in crystalline Form 2 was obtained in the form of a white solid.

$^1$H NMR (400 MHz, CDCl$_3$, ppm, inter alia) δ 6.51-6.44 (m, 1H), 5.78 (d, J=8 Hz, 1H), 5.38-5.20 (m, 2H), 3.48-3.40 (m, 1H), 3.36 (d, J=7 Hz, 1H), 3.25 (AB, J=15 Hz, 2H), 2.92-2.82 (m, 1H), 2.6-2.5 (m, 1H), 1.45 (s, 3H), 1.20 (s, 3H), 0.88 (d, J=7 Hz, 3H), 0.73 (d, J=8 Hz, 3H)

MS (ESI, g/mol): m/z 508 [M+H]$^+$

Example 5

14-O-{[(1R,2R,4R)-4-Amino-2-hydroxy-cyclohexyl-sulfanyl]-acetyl}-mutilin, crystalline Form 1

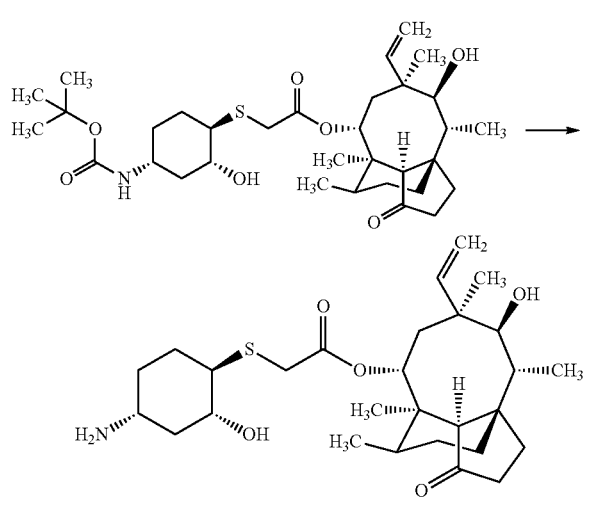

To a solution of 900 g of 14-O-{[(1R,2R,4R)-4-tert-butoxycarbonylamino-2-hydroxy-cyclohexyl-sulfanyl]-acetyl}-mutilin in 9 L of CH$_2$Cl$_2$ at 15 to 25° C. was added 1.8 L of TFA at 15 to 25° C. and the resulting solution was stirred for 2 h. Following reaction completion the reaction mixture was concentrated under vacuum and the concentration residue obtained was azeo-dried with a total of 9 L of CH$_2$Cl$_2$. The concentrate obtained was dissolved in 4.5 L of CH$_2$Cl$_2$, the solution obtained cooled to 0 to 5° C. and the pH was adjusted to pH 11 with aqueous 3.6 L K$_2$CO$_3$ (2.5M) solution. The biphasic mixture obtained was warmed to 15 to 20° C. and stirred for 5 to 10 minutes. The layers obtained were separated, the aqueous phase obtained was extracted with 1.8 L of CH$_2$Cl$_2$, the organic phases obtained were combined, washed with 2.3 L of H$_2$O, dried over Na$_2$SO$_4$ and concentrated to dryness under vacuum at <40° C. Crude 14-O-{[(1R, 2R,4R)-4-Amino-2-hydroxy-cyclohexyl-sulfanyl]-acetyl}-mutilin was obtained. Yield: 744 g For further purification the following procedure was applied:

To 744 g of crude 14-O-{[(1R,2R,4R)-amino-2-hydroxy-cyclohexyl-sulfanyl]-acetyl}-mutilin was added 2.23 L of THF and the resulting suspension was stirred at 15 to 25° C. for 60 min. To the mixture obtained 7.44 L of MTBE was added over 15 to 30 min, the suspension obtained was aged for 60 min and filtered under nitrogen. The collected solids were washed with a total of 3 L of MTBE and pulled dry on the filter under nitrogen for 1.5 h.

626 g of 14-O-{[(1R,2R,4R)-4-Amino-2-hydroxy-cyclohexyl-sulfanyl]-acetyl}-mutilin in crystalline Form 1 was obtained.

The $^1$H NMR pattern confirms the structure of 14-O-{[(1R, 2R,4R)-4-amino-2-hydroxy-cyclohexylsulfanyl]-acetyl}-mutilin. The NMR pattern for 14-O-{[(1R,2R,4R)-4-amino-2-hydroxy-cyclohexylsulfanyl]-acetyl}-mutilin is described in example 4.

Example 6

14-O-{[(1R,2R,4R)-4-[(2,2,2-Trifluoroacetyl)-amino-2-hydroxy-cyclohexyl-sulfanyl]-acetyl}-mutilin Procedure 1

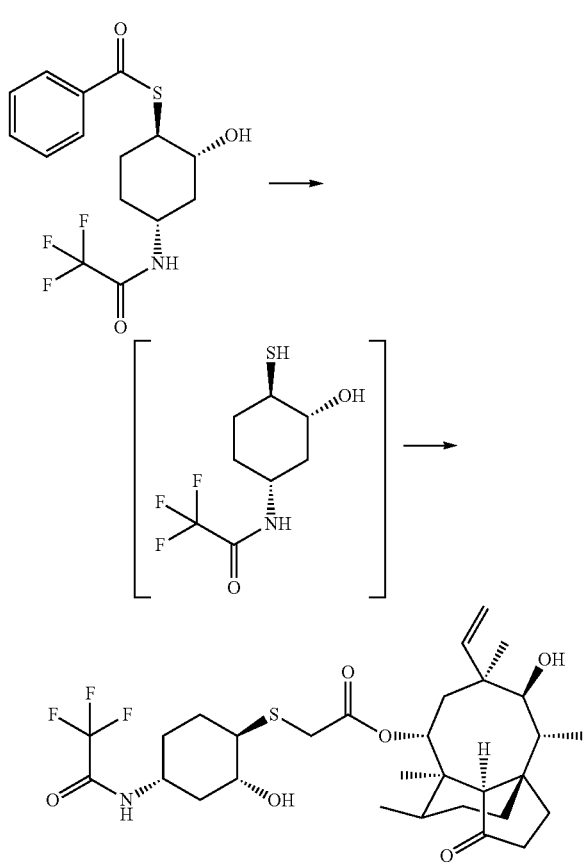

45.3 g of {(1R,2R,4R)-4-[(2,2,2-Trifluoro-acetyl)-amino]-2-hydroxy-cyclohexyl}-benzene-carbothioate and 453 ml of CH$_2$Cl$_2$ were charged to a flask and the mixture obtained was degassed at 15-25° C. with argon for 25 min. To the mixture obtained 12.79 g of hydrazine monohydrate was added dropwise followed by a 90.6 ml of CH$_2$Cl$_2$ line rinse. The mixture obtained was stirred at 20 to 25° C. for 2 h and the reaction was followed by TLC until completion. Upon completion of the reaction, the mixture obtained was cooled to 15 to 20° C. and washed with 158.6 ml of 2 M HCl solution. The phases obtained were separated, the aqueous phase obtained was returned to the vessel, 158.6 ml of saturated aqueous NaCl solution was added and the mixture obtained was back extracted with 2×78.8 ml of CH$_2$Cl$_2$. The combined organic phases obtained were washed with 90.6 ml of saturated aqueous NaCl solution and the organic layer obtained was concentrated to 2 volumes in vacuo at <40° C. To the concentrate obtained 226.5 ml of CH$_2$Cl$_2$ was added and the mixture obtained was concentrated to 2 volumes. To the concentrate obtained 362.4 ml of CH$_2$Cl$_2$ was added. A strip weight assay of the mixture obtained was carried out to determine the content of 2,2,2-trifluoro-N-[(1R,3R,4R)-3-hydroxy-4-mercapto-cyclohexyl]-acetamide and a yield of 27.1 g was determined.

The 2,2,2-trifluoro-N-[(1R,3R,4R)-3-hydroxy-4-mercapto-cyclohexyl]-acetamide solution (containing 27.1 g) obtained as described above was degassed with argon. 56.5 g of pleuromutilin tosylate was added, followed by a 54.3 ml of CH$_2$Cl$_2$ line rinse and the mixture obtained was stirred at 20 to 25° C. for 15 min. To the mixture obtained 34.0 g of DBU dissolved in 34 ml of CH$_2$Cl$_2$ was added over 30 min and the mixture obtained was stirred at 20 to 25° C. for 1 h until completion of the reaction. The mixture obtained was washed with 2×222.5 ml of 2M H$_2$SO$_4$ followed by 2×222.5 ml of 5% aqueous NaHCO$_3$ solution and the mixture obtained was concentrated to dryness in vacuo at 40° C. 72.7 g of 14-O-{[(1R,2R,4R)-[(2,2,2-Trifluoroacetyl)-amino-2-hydroxy-cyclohexyl-sulfanyl]-acetyl}-mutilin in the form of an off-white white foam was obtained.

$^1$H NMR (200 MHz, DMSO-d$_6$, ppm, inter alia) δ 9.31 (d, 1H), 6.15 (dd, J=17.8 Hz, J=11.1 Hz, 1H), 5.55 (d, J=7.8 Hz, 1H), 5.17-5.02 (m, 3H, H-20), 5.53 (d, J=5.8 Hz, 1H), 3.80-3.60 (m, 1H), 3.50-3.20 (m, 4H), 2.65-2.41 (m, 2H), 2.29-1.84 (m, 6H), 1.80-1.40 (m, 6H), 1.40-1.17 (m, 9H), 1.17-0.95 (m, 5H), 0.82 (d, J=6.8 Hz, 3H), 0.63 (d, J=5.8 Hz, 3H)

Procedure 2

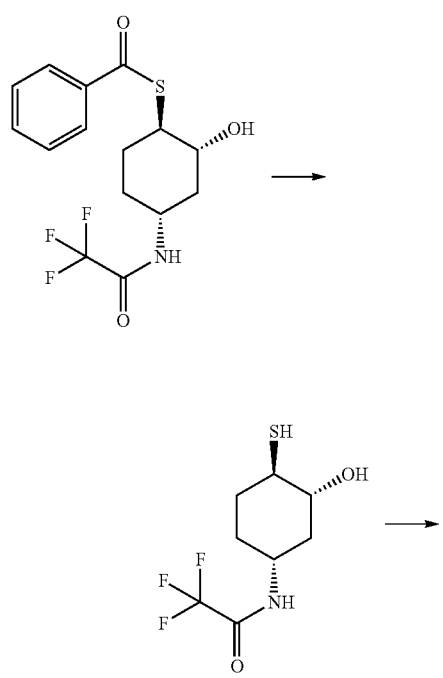

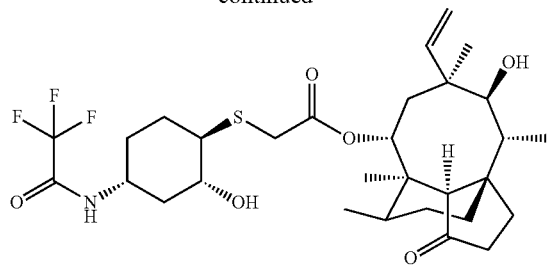

Step A: 2,2,2-Trifluoro-N-[(1R,3R,4R)-3-hydroxy-4-mercapto-cyclohexyl]-acetamide 5.79 g of {(1R,2R,4R)-4-[(2,2,2-Trifluoro-acetyl)-amino]-2-hydroxy-cyclohexyl}-benzene-carbothioate was dissolved in 81 ml of dichloromethane, 1.67 g (1.62 ml) of hydrazine hydrate was added and the resulting solution was stirred at rt for 3.5 h. To the mixture obtained 40 ml of 1M HCl was added and the biphasic mixture obtained was stirred vigorously for 10 min. Phases were separated and the organic phase obtained was washed with 40 ml of 1M HCl. The combined aqueous layers obtained were saturated with NaCl and washed with 30 ml of DCM; and the combined organic phases obtained were dried over anhydrous sodium sulfate and concentrated to dryness.

3.41 g of 2,2,2-trifluoro-N-[(1R,3R,4R)-3-hydroxy-4-mercapto-cyclohexyl]-acetamide in the form of colorless crystals was obtained.

$^1$H NMR (200 MHz, DMSO-d$_6$, ppm, inter alia) δ 9.31 (d, J=7.2 Hz, 1H), 5.12 (d, J=5.1 Hz, 1H), 3.82-3.6 (m, 1H), 3.24-3.09 (m, 1H), 2.62-2.5 (m, 1H), 2.40 (s, broad, 1H), 2.03-1.84 (m, 2H), 1.74-1.71 (m, 1H), 1.47-1.21 (m, 3H)

Step B: 14-O-{[(1R,2R,4R)-[(2,2,2-Trifluoro-acetyl)-amino]-2-hydroxy-cyclohexyl-sulfanyl]-acetyl}-mutilin 5.91 g of 2,2,2-trifluoro-N-[(1R,3R,4R)-3-hydroxy-4-mercapto-cyclohexyl]-acetamide and 11.78 g pleuromutilin tosylate were dissolved in 82.5 ml of DCM and the solution obtained was degassed with argon for 20 min. To the mixture obtained 6.91 g of DBU in 27.5 ml of DCM was added over 30 min. Upon completion of the reaction (TLC control) to the mixture obtained 25 ml of 2M HCl was added and the mixture obtained was stirred vigorously for 10 min. Phases obtained were separated, the organic phase obtained was washed with 12.5 ml 2M HCl and subsequently with 25 ml 5% sodium bicarbonate solution, dried over anhydrous sodium sulfate and filtered. From the filtrate obtained solvent was evaporated in vacuo.

16.8 g of 14-O-{[(1R,2R,4R)-4-[(2,2,2-trifluoro-acetyl)-amino]-2-hydroxy-cyclohexyl-sulfanyl]-acetyl}-mutilin was obtained in the form of a colorless foam. (the material contained DBU tosylate salt and residual DCM).

The $^1$H NMR pattern confirms the structure of 14-O-{[(1R,2R,4R)-4-[(2,2,2-Trifluoro-acetyl)-amino]-2-hydroxy-cyclohexyl-sulfanyl]-acetyl}-mutilin. The NMR pattern for 14-O-{[(1R,2R,4R)-4-[(2,2,2-Trifluoro-acetyl)-amino]-2-hydroxy-cyclohexyl-sulfanyl]-acetyl}-mutilin is described in example 6, procedure 1.

Example 7

14-O-{[(1R,2R,4R)-4-Amino-2-hydroxy-cyclohexyl-sulfanyl]-acetyl}-mutilin, crystalline Form 2

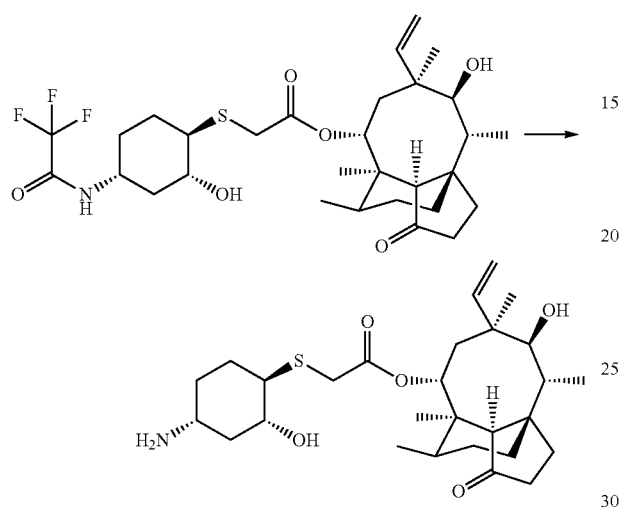

72.7 g of crude 14-O-{[(1R,2R,4R)-4-[(2,2,2-Trifluoro-acetyl)-amino-2-hydroxy-cyclohexyl-sulfanyl]-acetyl}-mutilin, 419.9 ml of methanol and 168 ml of water were charged to a flask and the mixture obtained was warmed to 40 to 45° C. To the mixture obtained 67.3 g of $K_2CO_3$ was added and the mixture obtained was stirred at 40 to 45° C. for 5 h. The reaction was followed by HPLC until completion. Upon completion of the reaction, the mixture obtained was cooled to 20 to 25° C., 588 ml of $CH_2Cl_2$ and 588 ml of 2 M phosphoric acid were added and the mixture obtained was stirred at 20 to 25° C. for 15 min. The mixture obtained was filtered biphasically, separated, and the organic layer obtained was extracted with 588 ml of 1 M phosphoric acid. The phases obtained were separated and to the combined aqueous (product) layers obtained was added 588 ml of $CH_2Cl_2$ and the mixture obtained was cooled to 10 to 15° C. To the mixture obtained 6 M NaOH was added dropwise at <25° C. until a pH of >9 was reached (275 ml required). The mixture obtained was filtered biphsaically and the layers obtained were separated. The organic (product) layer obtained was concentrated to approximately 5 volumes in vacuo at <40° C., 176 ml of $CH_2Cl_2$ was added and the mixture obtained was concentrated once more to 2 vols in vacuo at <40° C. To the concentrate obtained 323.5 ml of n-butanol was added dropwise, the mixture obtained was concentrated to 5 volumes in vacuo at <40° C. and the concentrate obtained was stirred at 20 to 25° C. for 2 h. The mixture obtained was filtered, the precipitate obtained was washed with 117.6 ml of n-butanol and the solid obtained was dried overnight in vacuo at 40° C. producing 44.2 g of 14-O-{[(1R,2R,4R)-4-amino-2-hydroxy-cyclohexylsulfanyl]-acetyl}-mutilin in crystalline Form 2.

44.2 g of crude 14-O-{[(1R,2R,4R)-4-amino-2-hydroxy-cyclohexylsulfanyl]-acetyl}-mutilin was charged to a clean vessel and 221 ml of n-butanol was added. The mixture obtained was heated to 88 to 92° C., stirred for 40 min, allowed to cool at a steady rate over 3 h to 40 to 45° C. and stirred for a further 2 h. The mixture obtained was filtered, washed with 44.2 ml of n-butanol followed by 44.2 ml of MTBE and dried in vacuo at <40° C.

37.6 g of crystalline 14-O-{[(1R,2R,4R)-4-amino-2-hydroxy-cyclohexylsulfanyl]-acetyl}-mutilin in crystalline Form 2 was obtained in the form of a white crystalline solid.

The $^1$H NMR pattern confirms the structure of 14-O-{[(1R,2R,4R)-4-amino-2-hydroxy-cyclohexylsulfanyl]-acetyl}-mutilin. The NMR pattern for 14-O-{[(1R,2R,4R)-4-amino-2-hydroxy-cyclohexylsulfanyl]-acetyl}-mutilin is described in example 4.

Example 8 tert-Butyl[(1R,3R,4R)-3-hydroxy-4-mercapto-cyclohexyl]-carbamate and tert-Butyl[(1S,3S,4S)-3-hydroxy-4-mercapto-cyclohexyl]-carbamate

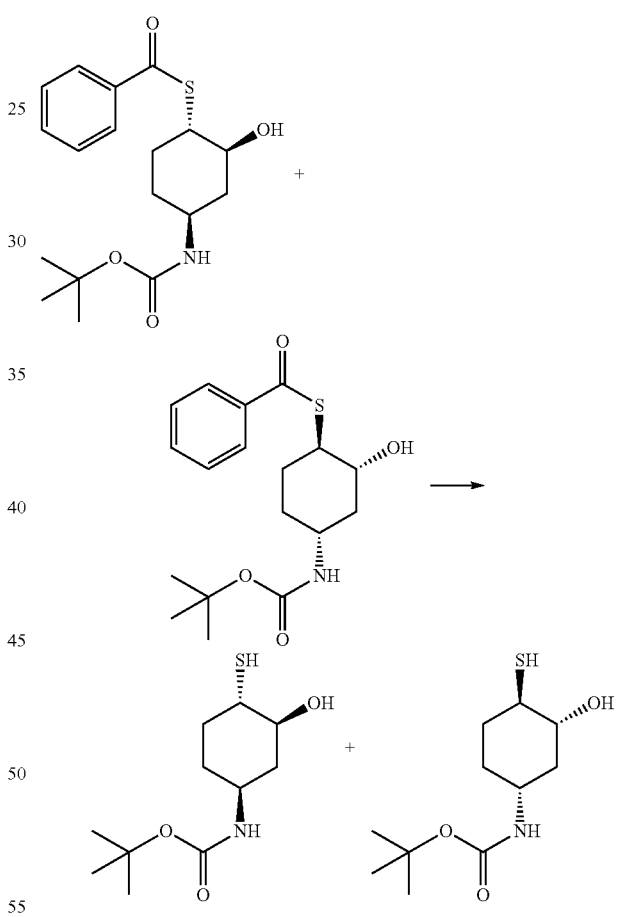

7.22 g of a mixture of {(1R,2R,4R)-4-[(tert-Butoxycarbonyl)-amino]-2-hydroxy-cyclohexyl}-benzene-carbothioate with {(1S,2S,4S)-4-[tert-Butoxycarbonyl)-amino]-2-hydroxy-cyclohexyl}-benzene-carbothioate and 72 ml of $CH_2Cl_2$ were charged to a flask and the mixture obtained was stirred at 15-25° C. The mixture obtained was degassed using argon for a period of 20 minutes. To the mixture obtained 0.72 g of 1,4-dithio-DL-threitol was added and 1.5 g of hydrazine monohydrate was added dropwise. The reaction was followed by TLC until completion. Upon completion of the reaction (2.5 h), to the mixture obtained 72 ml of 1 M phosphoric acid solution was added and the mixture obtained was stirred for 15 min. The phases obtained were separated, the lower organic phase was washed with 72 ml of 1 M phosphoric acid followed by 72 ml of 1% NaCl solution, dried over anhydrous magnesium sulfate (10 g), filtered and the solid rinsed through with 2×10 ml of $CH_2Cl_2$.

The mixture obtained was concentrated in vacuo at ≤40° C. 5.01 g of a mixture of tert-Butyl[(1R,3R,4R)-3-hydroxy-4-mercapto-cyclohexyl]-carbamate with tert-Butyl[(1S,3S,4S)-3-hydroxy-4-mercapto-cyclohexyl]-carbamate in the form of a white solid was obtained.

$^1$H NMR (200 MHz, DMSO-$d_6$, ppm, inter alia) δ 6.79 (d, J=7.8 Hz, 1H), 5.01 (d, J=5.6 Hz, 1H), 3.40-3.20 (m, 1H), 3.1-3.0 (m, 1H), 2.38 (d, J=3.8 Hz, 1H), 2.01-1.78 (m, 2H), 1.73-1.61 (m, 1H), 1.47-1.01 (m, 12H)

Example 9

14-O-{[(1R,2R,4R)-4-tert-Butoxycarbonylamino-2-hydroxy-cyclohexyl-sulfanyl]-acetyl}-mutilin and 14-O-{[(1S,2S,4S)-4-tert-Butoxycarbonylamino-2-hydroxy-cyclohexyl-sulfanyl]-acetyl}-mutilin

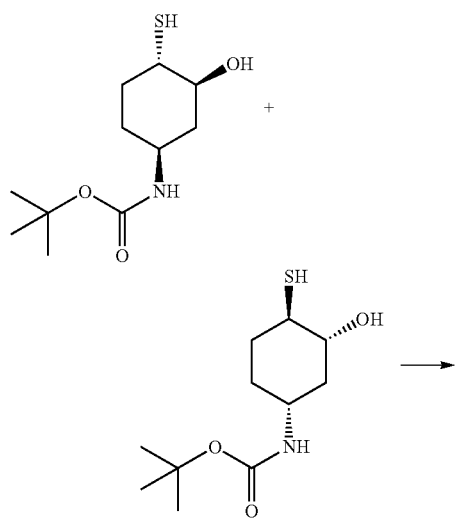

9.68 g of pleuromutilin tosylate and 101 ml of MTBE were charged to a flask and the mixture obtained was degassed at rt using argon for 5 to 10 minutes. To the mixture obtained 0.64 g of benzyl-tri-n-butylammonium chloride, 4.72 g of a mixture of tert-butyl[(1R,3R,4R)-3-hydroxy-4-mercapto-cyclohexyl]-carbamate with tert-butyl[(1S,3S,4S)-3-hydroxy-4-mercapto-cyclohexyl]-carbamate and 40 ml of aqueous 1 M NaOH solution were added with stirring. The mixture obtained was stirred at 20-25° C. and the reaction was followed by HPLC until completion. Upon completion of the reaction (1 h) the layers obtained were separated and the lower aqueous layer was removed. The organic phase obtained was washed with 40 ml of aqueous 1 M NaOH solution, 2×40 ml of 0.1 M phosphoric acid followed by 40 ml of 10% $NaHCO_3$ solution and 40 ml of $H_2O$. The organic liquors obtained were concentrated and dried in vacuo at ≤40° C. 11.88 g of a mixture of 14-O-{[(1R,2R,4R)-4-tert-butoxycarbonylamino-2-hydroxy-cyclohexyl-sulfanyl]-acetyl}-mutilin with 14-O-{[(1S,2S,4S)-4-tert-butoxycarbonylamino-2-hydroxy-cyclohexyl-sulfanyl]-acetyl}-mutilin was obtained in the form of a white foam (uncorrected for residual solvent)

$^1$H NMR (200 MHz, DMSO-$d_6$, ppm, inter alia) δ 6.79 (d, J=7.8 Hz, 1H), 6.22-6.07 (m, 1H), 5.55 (d, J=8 Hz, 1H), 5.12-4.96 (m, 3H), 4.54 (d, J=6 Hz, 1H), 3.55-3.24 (m, 4H), 2.54-2.50 (m, 1H), 2.41 (s, broad, 1H), 2.23-1.80 (m, 5H), 1.71-1.56 (m, 3H), 1.56-1.43 (m, 2H), 1.42-1.31 (m, 14H), 1.31-1.18 (m, 4H), 1.10-0.91 (m, 5H), 0.82 (d, J=6.6 Hz, 3H), 0.63 (d, J=5.8 Hz, 3H)

Example 10

14-O-{[(1R,2R,4R)-4-Amino-2-hydroxy-cyclohexyl-sulfanyl]-acetyl}-mutilin, crystalline Form 2

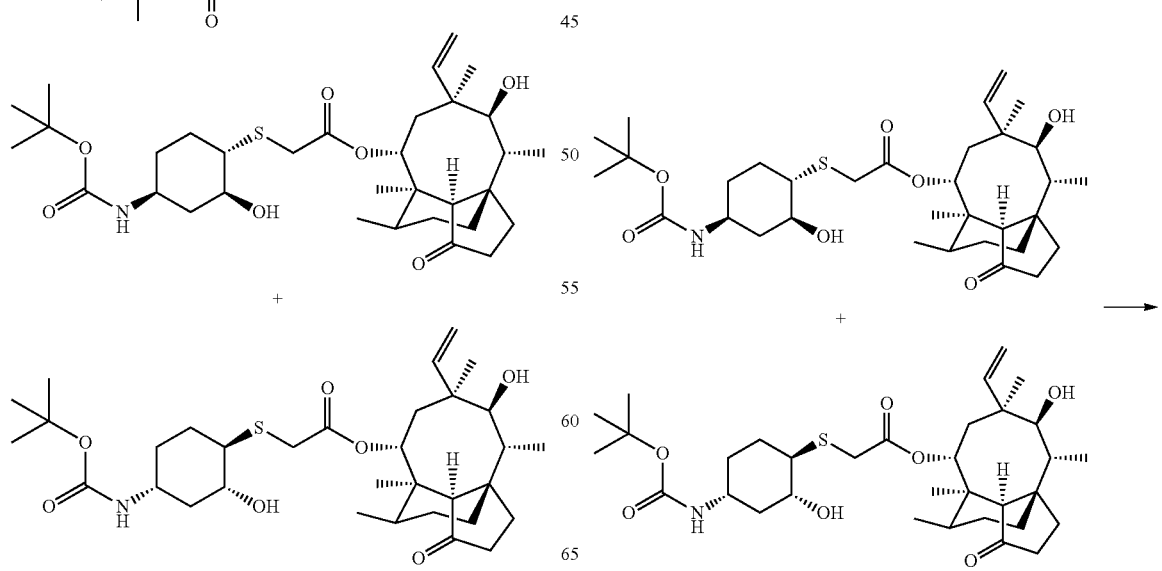

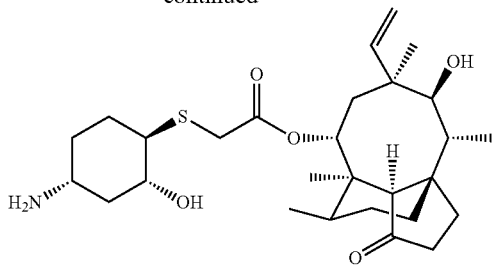

10.69 g of a mixture of 14-O-{[(1R,2R,4R)-4-tert-Butoxycarbonylamino-2-hydroxy-cyclohexyl-sulfanyl]-acetyl}-mutilin with 14-O-{[(1S,2S,4S)-4-tert-Butoxycarbonylamino-2-hydroxy-cyclohexyl-sulfanyl]-acetyl}-mutilin (corrected for residual solvent) and 24 ml of isopropanol were charged to a flask and the mixture obtained was stirred. To the mixture obtained 12 ml of 85% phosphoric acid was added and the mixture obtained was heated to 50° C. overnight. Upon completion of the reaction determined by HPLC the mixture obtained was cooled to rt and 119 ml of $CH_2Cl_2$ was added. The mixture obtained was cooled to 0 to 5° C. and 119 ml of 30% aqueous $K_2CO_3$ solution was added dropwise over 1 h. The mixture obtained was warmed to rt and settled. The phases formed were separated and the lower organic (product) layer obtained was removed. The aqueous layer (measured at pH 10) obtained was extracted with 119 ml of $CH_2Cl_2$ and the combined organic phases obtained were washed with 119 ml of $H_2O$. The organic phase obtained was concentrated to approximately 5 volumes, 59 ml of $CH_2Cl_2$ was added, and the mixture obtained was concentrated again to approximately 5 volumes. To the concentrate obtained 59 ml of dichloromethane was again added and the mixture obtained was concentrated to 2 volumes.

To the concentrate obtained 119 ml of di-isopropyl ether was added dropwise with stirring over a period of 1 h. A thick oily precipitate was obtained which became white crystals after approximately 1 h. The mixture obtained was stirred at 15 to 25° C. for 2 h, filtered, the precipitate obtained was washed with 24 ml of di-isopropyl ether and pulled dry on the filter. 8.28 g (uncorrected for residual solvent) of a mixture of 14-O-{[(1R,2R,4R)-4-amino-2-hydroxy-cyclohexylsulfanyl]-acetyl}-mutilin with 14-O-{[(1S,2S,4S)-4-amino-2-hydroxy-cyclohexylsulfanyl]-acetyl}-mutilin was obtained in the form of a solid (ratio 59:41). 8.28 g of the crude mixture obtained and 41 ml of n-butanol were charged to a flask and the mixture obtained was heated to 88 to 92° C. with stirring for 30 min. The mixture obtained was allowed to cool to rt over approximately 3 h. Precipitation was observed to begin at ~50° C. and the mixture obtained was stirred at rt overnight. The mixture obtained was filtered and the precipitate obtained was washed with 16.6 ml of n-butanol followed by 16.6 ml of MTBE and dried in vacuo at ≤40° C. 4.27 g of 14-O-{[(1R,2R,4R)-4-Amino-2-hydroxy-cyclohexylsulfanyl]-acetyl}-mutilin in the form of a white crystalline solid in crystalline Form 2 was obtained. The optical purity was 93% determined by chiral HPLC and the chemical purity was 99.14% area determined by RP HPLC.

In addition the comparison of the optical rotation of an authentic sample of 14-O-{[(1R,2R,4R)-4-Amino-2-hydroxy-cyclohexylsulfanyl]-acetyl}-mutilin with the optical rotation of 14-O-{[(1R,2R,4R)-4-Amino-2-hydroxy-cyclohexylsulfanyl]-acetyl}-mutilin obtained as described above confirmed the chiral purity as well; $([\alpha]_D(CHCl_3)=+24.9°$ versus +25.9° for the authentic sample)

The resultant mother liquors from the n-butanol recrystallization were evaporated to dryness to give a white foam. 3.67 g of a mixture of 14-O-{[(1S,2S,4S)-4-Amino-2-hydroxy-cyclohexylsulfanyl]-acetyl}-mutilin with 14-O-{[(1R,2R,4R)-4-Amino-2-hydroxy-cyclohexylsulfanyl]-acetyl}-mutilin were obtained (ratio 84.0:16.0; determined by chiral HPLC)

The $^1H$ NMR pattern confirms the structure of 14-O-{[(1R,2R,4R)-4-amino-2-hydroxy-cyclohexylsulfanyl]-acetyl}-mutilin. The NMR pattern for 14-O-{[(1R,2R,4R)-4-amino-2-hydroxy-cyclohexylsulfanyl]-acetyl}-mutilin is described in example 4.

Example 11

14-O-{[(1R,2R,4R)-4-Amino-2-hydroxy-cyclohexylsulfanyl]-acetyl}-mutilin acetate, crystalline Form A

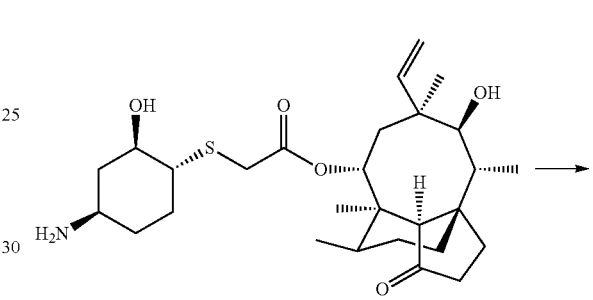

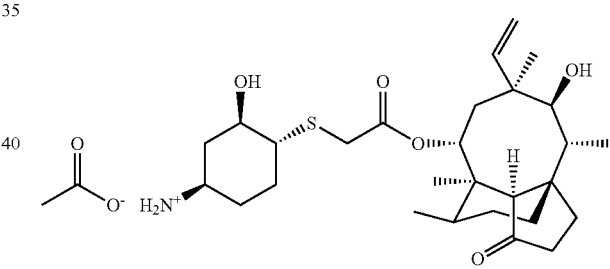

To a suspension of 615 g 14-O-{[(1R,2R,4R)-4-amino-2-hydroxy-cyclohexyl-sulfanyl]-acetyl}-mutilin in 12.3 L of methyl acetate at 50 to 55° C. was added 62 ml of water and the resulting hazy solution was clarified through GF filter paper. The filtrates obtained were heated to 50 to 55° C. (clear solution), 123 ml acetic acid was added, the resultant mixture was stirred at 50 to 55° C. for 25 minutes, cooled to 15 to 25° C. over 80 minutes and further cooled to 0 to 5° C. over 60 min. The resulting suspension was aged at 0 to 5° C. for 80 minutes, filtered and the filter cake was washed with 3.08 L of methyl acetate. The filter cake was pulled dry on the filter under nitrogen for 2 hours. 574.1 g of 14-O-{[(1R,2R,4R)-4-Amino-2-hydroxy-cyclohexyl-sulfanyl]-acetyl}-mutilin in the form of an acetate in the form of a crystalline, fine white powder in crystalline Form A was obtained.

The $^1H$ NMR pattern confirms the structure of 14-O-{[(1R,2R,4R)-4-Amino-2-hydroxy-cyclohexyl-sulfanyl]-acetyl}-mutilin acetate. The NMR pattern for 14-O-{[(1R,2R,4R)-4-

Amino-2-hydroxy-cyclohexyl-sulfanyl]-acetyl}-mutilin acetate is described in example 12.

Example 12

14-O-{[(1R,2R,4R)-4-Amino-2-hydroxy-cyclohexyl-sulfanyl]-acetyl}-mutilin acetate, crystalline Form B

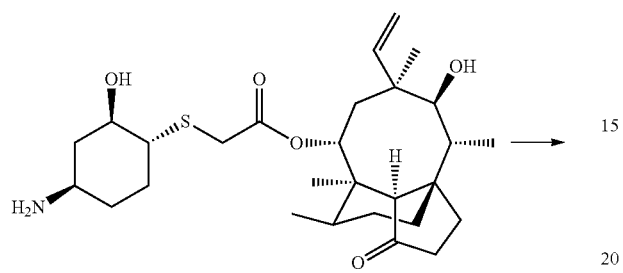

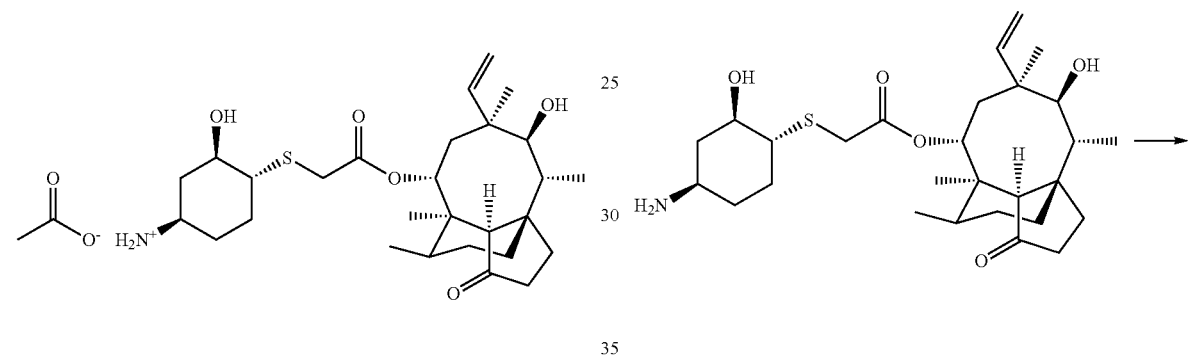

Procedure 1

To a suspension of 3260 g of 14-O-{[(1R,2R,4R)-4-amino-2-hydroxy-cyclohexyl-sulfanyl]-acetyl}-mutilin in 56.8 L of isopropyl acetate were added 10 g of seed crystals of 14-O-{[(1R,2R,4R)-4-amino-2-hydroxy-cyclohexyl-sulfanyl]-acetyl}-mutilin in crystalline Form B. The crystallization occurs also without adding the seed crystals. The resulting suspension was stirred at 20 to 25° C. for ≥10 min. To the mixture obtained was added 353 ml of acetic acid, and the mixture obtained was stirred at 20 to 25° C. for 1 h and tested for completion and polymorphic form by XRPD. The suspension obtained was stirred for a further 1 h at 20 to 25° C., filtered, and the filter cake obtained was twice washed with 2.84 L each of isopropyl acetate. The solid obtained was dried under vacuum at 50° C. for at least 12 h. 3.15 kg of 14-O-{[(1R,2R,4R)-4-Amino-2-hydroxy-cyclohexyl-sulfanyl]-acetyl}-mutilin acetate in the form of a crystalline white solid in crystalline Form B was obtained.

Procedure 2

2.00 g of 14-O-{[(1R,2R,4R)-4-Amino-2-hydroxy-cyclohexyl-sulfanyl]-acetyl}-mutilin was dissolved in 6 ml of methanol. To the mixture obtained 0.338 ml of acetic acid was added in one portion and the solution obtained was stirred for 15 min. To the mixture obtained 30 ml of isopropyl acetate was added over 30 min and the resulting suspension was stirred during 30 min. The slurry obtained was heated to 30° C., 15 volumes were distilled off and 3 strips (of 3 volumes each) of isopropyl acetate were performed. The slurry obtained was filtered and the white precipitate obtained was isolated, washed with isopropylacetate and dried overnight. 1.74 g of {[(1R,2R,4R)-4-Amino-2-hydroxy-cyclohexyl-sulfanyl]-acetyl}-mutilin acetate in the form of a white crystalline solid in crystalline Form B was obtained.

$^1$H NMR (500 MHz, DMSO-$d_6$, ppm, inter alia) δ 6.16-6.10 (m, 1H), 5.54 (d, J=8.3 Hz, 1H), 5.09-5.02 (m, 2H), 3.42 (d, J=6 Hz, 1H), 3.37 (AB, J=15 Hz, 2H), 3.29-3.25 (m, 1H), 2.77-2.67 (m, 1H), 2.55-2.5 (m, 1H), 2.40 (s, broad, 1H), 2.23-2.12 (m, 1H), 2.12-2.03 (m, 3H), 2.03-1.95 (m, 1H), 1.94-1.85 (m, 1H), 1.77 (s, 3H), 1.77-1.71 (m, 1H), 1.7-1.57 (m, 2H), 1.52-1.43 (m, 1H), 1.43-1.37 (m, 1H), 1.36 (s, 3H), 1.37-0.96 (m, 10H), 0.81 (d, J=7 Hz, 3H), 0.62 (d, J=7 Hz, 3H)

Example 13

14-O-{[(1R,2R,4R)-4-Amino-2-hydroxy-cyclohexyl-sulfanyl]-acetyl}-mutilin L-lactate, crystalline Form 1

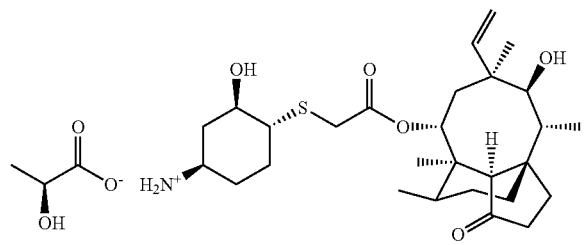

22 g of 14-O-{[(1R,2R,4R)-4-Amino-2-hydroxy-cyclohexyl-sulfanyl]-acetyl}-mutilin and 1.1 L of EtOAc were charged to a vessel. The suspension obtained was heated to 50° C. and held until dissolution. To the mixture obtained 1 equivalent of 98% L-lactic acid was added and the mixture obtained was gradually cooled to 25° C. over 3 h.

Optionally 14-O-{[(1R,2R,4R)-4-Amino-2-hydroxy-cyclohexyl-sulfanyl]-acetyl}-mutilin L-lactate seed crystals were added. Crystallization also occurs without seed crystals.

The resultant suspension was stirred at 20-25° C. overnight and further cooled to 5° C. for 1 h. The precipitate obtained was isolated by filtration and dried in vacuo at 40° C. overnight. 23.7 g of 14-O-{[(1R,2R,4R)-4-Amino-2-hydroxy-cyclohexyl-sulfanyl]-acetyl}-mutilin L-lactate in crystalline Form 1 was obtained.

$^1$H NMR (400 MHz, DMSO-$d_6$, ppm, inter alia) δ 6.13 (dd, J=11 and 18 Hz, 1H), 5.54 (d, J=8 Hz, 1H), 5.10-5.01 (m, 2H), 4.53 (d, broad, 1H), 3.60 (dd, J=7 and 14 Hz, 1H), 3.40 (AB, J=15 Hz, 2H), 2.93 (m, 1H), 2.55-2.48 (m, 1H), 2.39 (s, broad, 1H), 1.36 (s, 3H), 1.09 (d, J=7 Hz, 3H), 1.04 (s, 3H), 0.81 (d, J=7 Hz, 3H), 0.61 (d, J=7 Hz, 3H).

Example 14

14-O-{[(1R,2R,4R)-4-Amino-2-hydroxy-cyclohexyl-sulfanyl]-acetyl}-mutilin hydrogenmaleate, crystalline Form 1

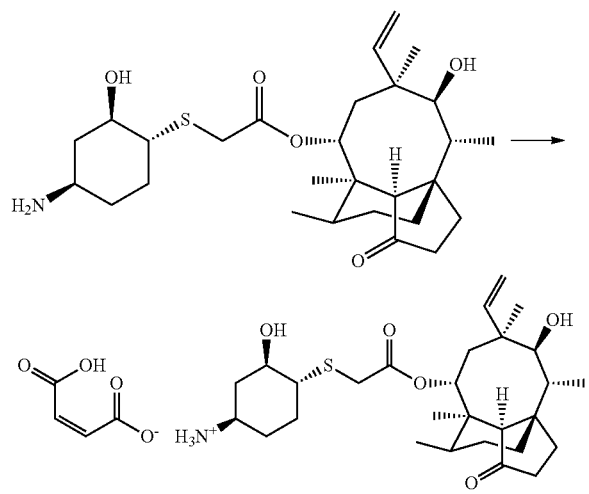

5.5 g of 14-O-{[(1R,2R,4R)-4-Amino-2-hydroxy-cyclohexyl-sulfanyl]-acetyl}-mutilin and 110 ml of EtOAc were charged to a flask. The suspension obtained was heated to 80° C. and held until dissolution. To the mixture obtained 10.8 ml of 1M maleic acid in THF was charged, and the mixture obtained was allowed to cool to rt overnight with stirring.

Optionally 14-O-{[(1R,2R,4R)-4-Amino-2-hydroxy-cyclohexyl-sulfanyl]-acetyl}-mutilin hydrogenmaleate seed crystals were added. Crystallization occurs also without seed crystals. 6.16 g of 14-O-{[(1R,2R,4R)-4-amino-2-hydroxy-cyclohexyl-sulfanyl]-acetyl}-mutilin in the form of a crystalline hydrogenmaleate salt in crystalline Form 1 was isolated by filtration and dried for 6 h in vacuo.

$^1$H NMR (400 MHz, DMSO-d$_6$, ppm, inter alia) δ 6.13 (dd, J=11 and 18 Hz, 1H), 6.00 (s, 2H), 5.54 (d, J=8 Hz, 1H), 5.10-5.01 (m, 2H), 4.54 (d, J=6 Hz, 1H), 3.40 (AB, J=15 Hz, 2H), 3.05 (m, 1H), 2.56-2.49 (m, 1H), 2.40 (s, broad, 1H), 1.36 (s, 3H), 1.05 (s, 3H), 0.81 (d, J=7 Hz, 3H), 0.61 (d, J=7 Hz, 3H).

The process to exchange the amine protecting group R in a compound of formula I is shown in REACTION SCHEME 3 below:

REACTION SCHEME 3

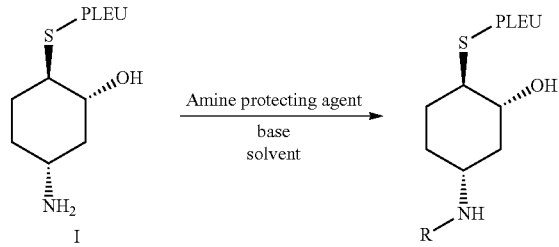

In REACTION SCHEME 3 R represents an amino protecting group as defined above.

Example 15

14-O-{[(1R,2R,4R)-4-[(2,2,2-Trifluoroacetyl)-amino-2-hydroxy-cyclohexyl-sulfanyl]-acetyl}-mutilin

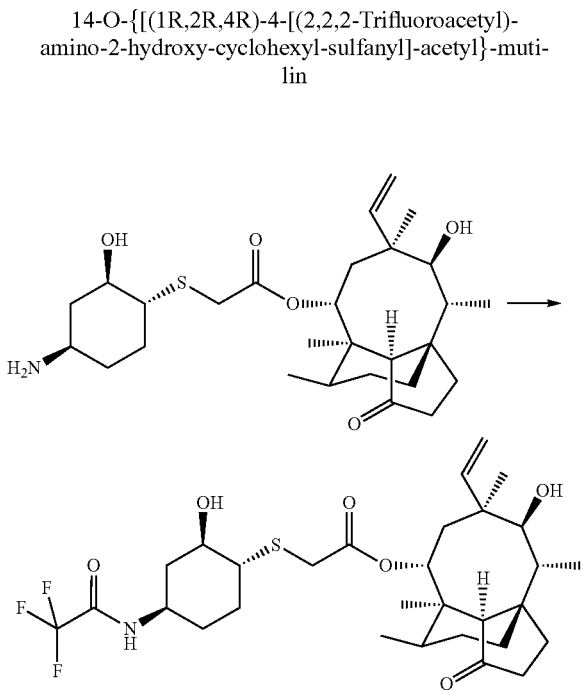

1 g of 14-O-{[(1R,2R,4R)-4-Amino-2-hydroxy-cyclohexyl-sulfanyl]-acetyl}-mutilin and 10 ml of DCM were charged to a flask at RT and the mixture obtained was stirred. To the mixture obtained 0.41 ml of triethylamine were added dropwise, followed by 0.29 ml of trifluoroacetic anhydride and the mixture obtained was stirred until reaction completion (determined by by TLC). The mixture obtained was washed with 10 ml of 0.1 M HCl followed by 10 ml of 5% NaHCO$_3$ and 10 ml of water and concentrated to dryness. 1.20 g of 14-O-{[(1R,2R,4R)-4-[(2,2,2-Trifluoroacetyl)-amino-2-hydroxy-cyclohexyl-sulfanyl]-acetyl}-mutilin was obtained in the form of a foam.

The $^1$H NMR pattern confirms the structure of 14-O-{[(1R,2R,4R)-4-[(2,2,2-Trifluoroacetyl)-amino-2-hydroxy-cyclohexyl-sulfanyl]-acetyl}-mutilin. The NMR pattern for 14-O-{[(1R,2R,4R)-4-[(2,2,2-Trifluoroacetyl)-amino-2-hydroxy-cyclohexyl-sulfanyl]-acetyl}-mutilin is described in example 6.

Example 16

14-O-{[(1R,2R,4R)-4-ethoxycarbonylamino-2-hydroxy-cyclohexyl-sulfanyl]-acetyl}-mutilin

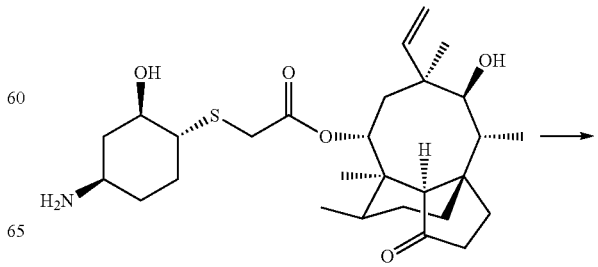

-continued

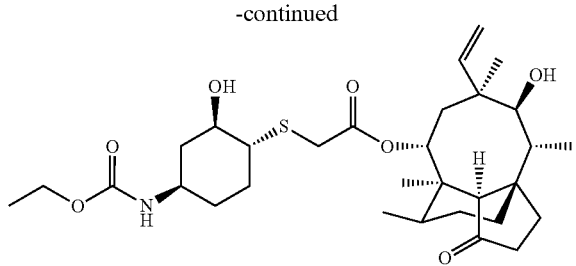

1 g of 14-O-{[(1R,2R,4R)-4-Amino-2-hydroxy-cyclohexyl-sulfanyl]-acetyl}-mutilin and 10 ml of DCM were charged to a flask at RT and the mixture obtained was stirred. To the mixture obtained 0.41 ml of triethylamine was added dropwise, followed by 0.2 ml of ethyl chloroformate and the mixture obtained was stirred until reaction completion (determined by by TLC). The mixture obtained was washed with 10 ml of 0.1 M HCl followed by 10 ml of 5% NaHCO₃ and 10 ml of water and concentrated to dryness.

1.05 g of 14-O-{[(1R,2R,4R)-4-ethoxycarbonylamino-2-hydroxy-cyclohexyl-sulfanyl]-acetyl}-mutilin was obtained in the form of a foam.

$^1$H NMR (400 MHz, DMSO-d-$_6$, ppm, inter alia) δ 7.07 (d, J=7.6 Hz, 1H), 6.16 (dd, J=17.6 Hz, J=11.0 Hz, 1H), 5.55 (d, 1H, J=8.0 Hz), 5.13-4.96 (m, 3H), 4.54 (d, 1H, J=5.8 Hz), 4.00-3.89 (q, 2H), 3.56-3.14 (m, 5H), 2.51-2.36 (m, 2H), 2.18-1.80 (m, 5H), 1.80-1.40 (m, 5H), 1.40-0.88 (m, 17H), 0.82 (d, J=6.8 Hz, 3H), 0.63 (d, J=5.8 Hz, 3H)

Example 17

14-O-{[(1R,2R,4R)-2-hydroxy-4-(phtalimido-N-yl)-cyclohexyl-sulfanyl]-acetyl}-mutilin

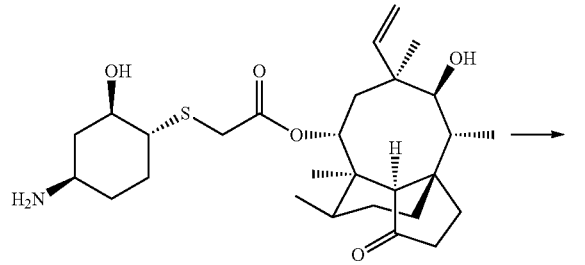

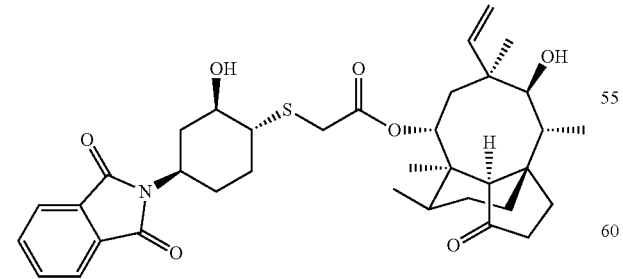

1 g of 14-O-{[(1R,2R,4R)-4-Amino-2-hydroxy-cyclohexyl-sulfanyl]-acetyl}-mutilin and 40 ml of toluene were charged to a flask at RT and the mixture obtained was stirred. To the mixture obtained 0.41 ml of triethylamine were added dropwise, followed by 0.30 g of phthalic anhydride and the mixture obtained was heated to reflux and the water was removed under Dean-Stark conditions, until reaction completion (determined by HPLC). The mixture obtained was washed with 10 ml of 0.1 M HCl followed by 10 ml of 5% NaHCO₃ and 10 ml of water, dried over sodium sulfate and concentrated to dryness.

0.87 g of 14-O-{[(1R,2R,4R)-2-hydroxy-4-(phtalimido-N-yl)-cyclohexyl-sulfanyl]-acetyl}-mutilin was obtained in the form of pale white crystals.

$^1$H NMR (400 MHz, DMSO-d-$_6$, ppm, inter alia) δ 7.9-7.7 (m, 4H), 6.17 (dd, J=17.6 Hz, J=11.2 Hz, 1H), 5.58 (d, 1H, J=7.8 Hz), 5.16-5.06 (m, 3H), 4.54 (d, 1H, J=6.0 Hz), 4.13-4.01 (m, 1H), 3.62-3.29 (m, 4H), 2.69-2.60 (m, 1H), 2.43 (m, 1H), 2.30-1.80 (m, 8H), 1.80-1.15 (m, 12H), 1.1-0.9 (m, 4H), 0.83 (d, J=6.6 Hz, 3H), 0.65 (d, J=5.8 Hz, 3H)

The process to the starting material of formula IVa useful for the production of compounds of formula IIIa is summarized in Reaction Scheme 4 below.

REACTION SCHEME 4

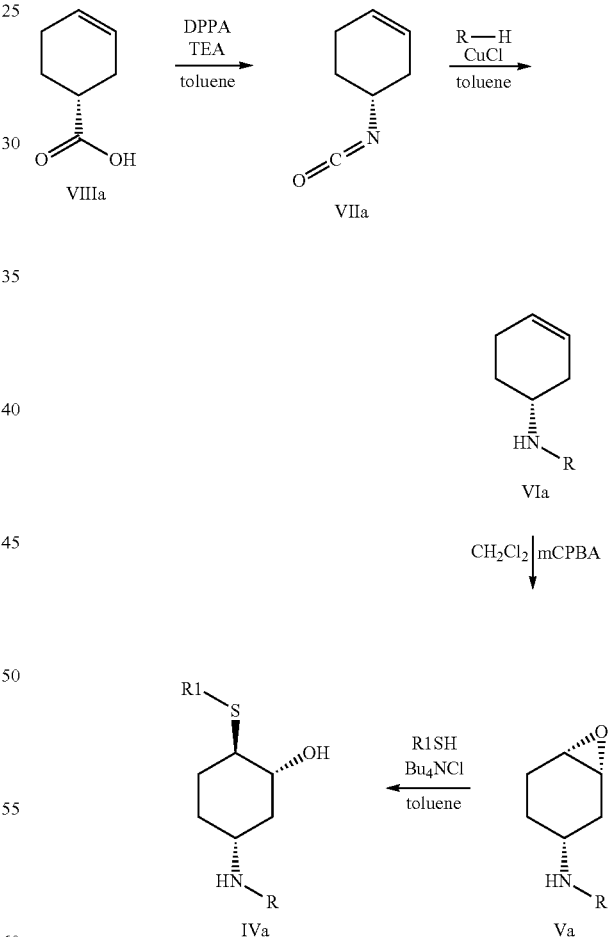

In REACTION SCHEME 4 R represents an amino protecting group and R₁ represents a sulfur protecting group and are as defined above.

Example 18

{(1R,2R,4R)-4-[(tert-Butoxycarbonyl)-amino]-2-hydroxy-cyclohexyl}-benzene-carbothioate Step A: tert-Butyl cyclohex-3-enyl-1(R)-carbamate A. Salt Formation of cyclohex-3-ene-1-carboxylic acid

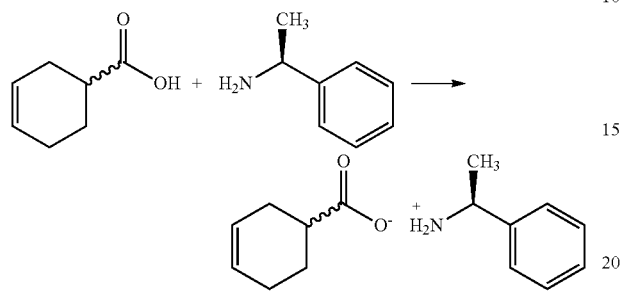

1000 g of racemic cyclohex-3-ene-1-carboxylic acid was charged to a flask and 5 volumes of acetone was added. The mixture obtained was stirred, heated to 55 to 60° C. and stirred for 30 min. To the mixture obtained 960.5 g of (S)-(−)-α-methylbenzylamine in 2 volumes of acetone were added dropwise over approximately 25 min. A clear, orange solution was obtained and cooled slowly. Crystallization started at 53° C. (after 30 min). Full crystallization occurred after ~1 h at 49° C. The mixture obtained was cooled to rt over a further 3 h with an ice bath then stirred at rt for a further 1.5 h. The precipitate obtained was filtered off and washed with acetone. An α-methylbenzylamine salt of cyclohex-3-ene-1-carboxylic acid as set out in the reaction scheme above was obtained.

Yield (wet): 1966.9 g; optical rotation: $^{20}[\alpha]_D$=+8.05° (c=1, MeOH)

B. Salt Resolution 1966.9 g (wet) of a salt as set out under step A and 3.8 volumes of acetone were charged to a 10 L vessel and the mixture obtained was heated to 55 to 60° C. When the product had dissolved, the mixture obtained was stirred for a further 15 min and then slowly cooled to rt. Crystallization started after 1 h 10 min (53° C.). The mixture obtained was cooled to 20 to 25° C. over 4.5 h and stirred at rt for a further 1.5 h. The precipitate obtained was filtered off and washed with acetone. An α-methylbenzylamine salt of cyclohex-3-ene-1-carboxylic acid wherein the R-isomer was enriched was obtained.

Yield (wet): 1143 g; optical rotation: $^{20}[\alpha]_D$=+20.65° (c=1, MeOH)

Step B. was repeated until a required optical rotation ($^{20}[\alpha]_D$>40°) was achieved.

C. Cyclohex-3-ene-1(R)-carboxylic acid

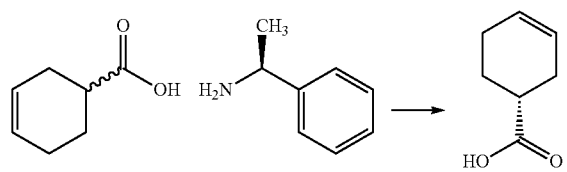

579.6 g of cyclohex-3-ene-1(R)-carboxylic acid (S)-(−)-α-methylbenzylamine salt and 5 volumes of MTBE were charged to a flask at 20-25° C. and the mixture obtained was stirred. To the mixture obtained 10 volumes of 1M HCl were added, the mixture obtained was stirred for 5-10 min and two layers were formed. The layers obtained were separated and the aqueous layer was extracted with MTBE. The organic layers obtained were combined and washed with brine. The organic phase obtained was dried over Na$_2$SO$_4$, filtered, and the filter cake obtained was washed with MTBE. From the filtrate obtained solvent was removed in vacuo. Cyclohex-3-ene-1(R)-carboxylic acid in the form of a clear oil was obtained.

Yield: 301.78 g

Optical rotation $^{20}[\alpha]_D$=+83.1° (c=1, CHCl$_3$)

Cyclohex-3-ene-1(R)-carboxylic acid may be obtained in analogy to the method disclosed in Schwartz, H. M.; et al. JACS 1978, 100, 5199-5203.

D. Curtius Rearrangement to Obtain tert-butyl cyclohex-3-enyl-(R)-carbamate

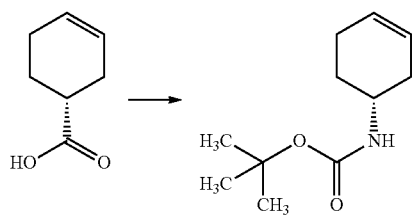

305 g of cyclohex-3-ene-1(R)-carboxylic acid and 10 volumes of toluene were charged to a flask at 20-25° C. and the mixture obtained was stirred. To the mixture obtained 1.1 equivalents of triethylamine were added dropwise over 15 min and the mixture obtained was stirred for a further 20 min. To the mixture obtained 1.05 equivalents of DPPA were added dropwise over approximately 20 min and the temperature raised to 95° C. (exothermic reaction) with vigorous gas evolution. The mixture obtained was stirred for 15 min and heated to reflux. Progress of the reaction was followed by $^1$H NMR measurements until completion. The mixture obtained was cooled to 80° C. over 35 min and 5 equivalents of tert-butanol were added dropwise over 10 min, followed by 7.65 g of CuCl. The mixture obtained was warmed to 100° C. and stirred for a further 40 min. Progress of the reaction was followed by $^1$H NMR measurements until completion. The mixture obtained was cooled and 5 volumes of aqueous, saturated NaHCO$_3$ solution were added over 10 min. The mixture obtained was stirred for 20 min and left overnight. The mixture obtained was filtered and the residual solid was washed twice with toluene. The organic layers were separated and the aqueous layer was washed twice with toluene. All organic layers obtained were combined, washed with H$_2$O and solvent was removed in vacuo. tert-Butyl cyclohex-3-enyl-1(R)-carbamate was obtained in the form of a light brown solid. Crude Yield: 479.7 g The crude tert-Butyl cyclohex-3-enyl-1(R)-carbamate obtained was subjected to chromatography. For 160 g of crude product the column was packed with 1.5 Kg silica gel, using 2.5 L of cyclohexane, and topped with sand. The crude product was loaded in 0.8 L of 5% EtOAc/cyclohexane. The column was flashed with the following gradient system, a discrete fraction being collected each time:

2% EtOAc/cyclohexane (9×0.8 L fractions)
5% EtOAc/cyclohexane (7×0.8 L fractions)
10% EtOAc/cyclohexane (4×0.8 L fractions)
Overall yield after chromatography: 81.3% of theory
$^1$H NMR (CDCl$_3$, 500 MHz, ppm): δ 5.64-5.67 (m, 1H), 5.56-5-60 (m, 1H), 4.54 (s, broad, 1H), 3.77 (s, broad, 1H), 2.32-2.34 (m, 1H), 2.07-2.17 (m, 2H), 1.81-1.87 (m, 2H), 1.48-1.56 (m, 1H), 1.44 (s, 9H)
$^{13}$C NMR (CDCl$_3$, 500 MHz, ppm):): δ 155.3, 126.9, 124.5, 79.1, 45.7, 32.1, 28.4, 23.6

Step B: tert-Butyl(1R,3R,6S)-(7-oxa-bicyclo[4.1.0]hept-3-yl)-carbamate

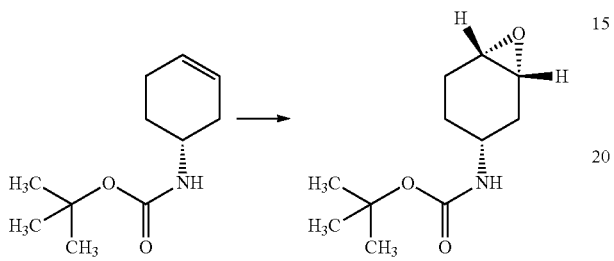

4500 g of mCPBA (70%) and 24 L of CH$_2$Cl$_2$ were charged to a vessel and the mixture obtained was cooled to 15° C. 3000 g of tert-butyl cyclohex-3-enyl-1(R)-carbamate in 4.5 L of CH$_2$Cl$_2$ was added dropwise over approximately 30 min maintaining the temperature at 15 to 25° C. To the mixture obtained 1.5 L of CH$_2$Cl$_2$ was added and the mixture obtained was stirred at 20 to 25° C. for 1 h and heated to reflux (40° C.) for 2 h. Upon completion of the reaction ($^1$H NMR control), the mixture was cooled to −5 to 0° C., stirred overnight and the solid precipitate obtained was filtered off and washed with CH$_2$Cl$_2$. The resultant filtrate was washed with 10% aqueous sodium thiosulfate solution in order to remove peroxides, 10% aqueous NaHCO$_3$ solution until a pH>7 was achieved in the aqueous phase, and water. The organic phase obtained was concentrated to minimal volume and 15 L of toluene was added and the mixture obtained was concentrated again to minimal volume. This strip process was repeated two more times. 2.63 Kg (2.05 Kg yield corrected for residual mCBA and toluene) of tert-Butyl(1R,3R,6S)-(7-oxa-bicyclo[4.1.0]hept-3-yl)-carbamate in the form of a solution in toluene was obtained.

$^1$H NMR (200 MHz, CDCl$_3$, ppm) δ 4.85 (d, J=7 Hz, 1H), 3.6-3.54 (m, 1H), 3.10 (s, broad, 2H), 2.23-1.99 (m, 2H), 1.92-1.67 (m, 2H), 1.54-1.27 (m, 11H)

Step C: {(1R,2R,4R)-4-[(tert-Butoxycarbonyl)-amino]-2-hydroxy-cyclohexyl}-benzene-carbothioate

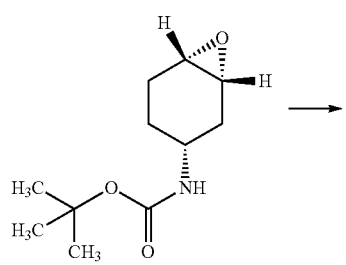

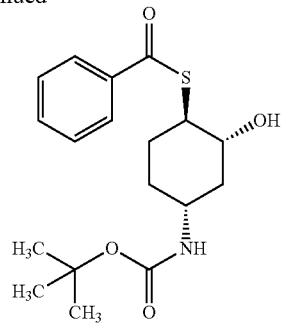

2630 g (2050 g corrected) of tert-butyl(1R,3R,6S)-(7-oxa-bicyclo[4.1.0]hept-3-yl)-carbamate in form of a solution in toluene (solution weight: 15.44 Kg) from step B above and 3.1 L of toluene were charged to a vessel and the mixture obtained was stirred at 15-25° C. To the mixture obtained 1.44 L of thiobenzoic acid (10%) was added dropwise. The temperature was kept below 30° C. Further 1.9 L of toluene and 85.3 g of tetrabutylammonium chloride monohydrate in one portion were added, external temperature control was stopped, and the mixture obtained was subjected to exotherm reaction. The mixture obtained was heated to 40-45° C. and stirred for 4 h. Upon completion of the reaction (TLC and $^1$H NMR-control), the mixture obtained was cooled to 15 to 20° C. and washed twice with 5% aqueous NaHCO$_3$ solution followed twice with H$_2$O. The organic layer obtained was concentrated in vacuo to minimum volume. 10.25 L of toluene was added and the mixture obtained was again concentrated to minimum volume. That process was repeated and the dry weight obtained was determined. All subsequent reslurry volumes are relatived to this weight.

To the crude concentration residue obtained 0.5 volumes of toluene were added under stirring and the mixture obtained was stirred at 15 to 25° C. for 30 min. To the mixture obtained 0.5 volumes of heptane was added dropwise over 15 min and the mixture obtained stirred at 15 to 25° C. for 40 min. The solid obtained was filtered and washed with 0.25 volumes of toluene-heptane (1:1), followed by a slurry wash with 0.5 volumes of toluene-heptane (1:1), followed by a displacement wash with 0.25 volumes of toluene-heptane (1:1).

This procedure reduced the amount of unwanted regioisomer and thiobenzoic acid to undetectable (by $^1$H NMR). The solid obtained was isolated and dried in vacuo at 30° C. 1090 g of {(1R,2R,4R)-4-[tert-Butoxycarbonyl)-amino]-2-hydroxy-cyclohexyl}-benzene-carbothioate in the form of a white solid was obtained.

$^1$H NMR (200 MHz, DMSO-d$_6$, ppm) δ 7.92-7.87 (m, 2H), 7.71-7.63 (m, 1H), 7.58-7.49 (m, 2H), 6.85 (d, J=8 Hz, 1H), 5.11 (d, J=5.6 Hz, 1H), 3.49-3.25 (m, 3H), 2.12-1.95 (m, 2H), 1.79-1.69 (m, 1H), 1.54-1.14 (m, 12H)

An alternative process (telescoping) to obtain the starting material of formula IVa which is useful for the production of compounds of formula IIIa is summarized in REACTION SCHEME 5 below:

REACTION SCHEME 5

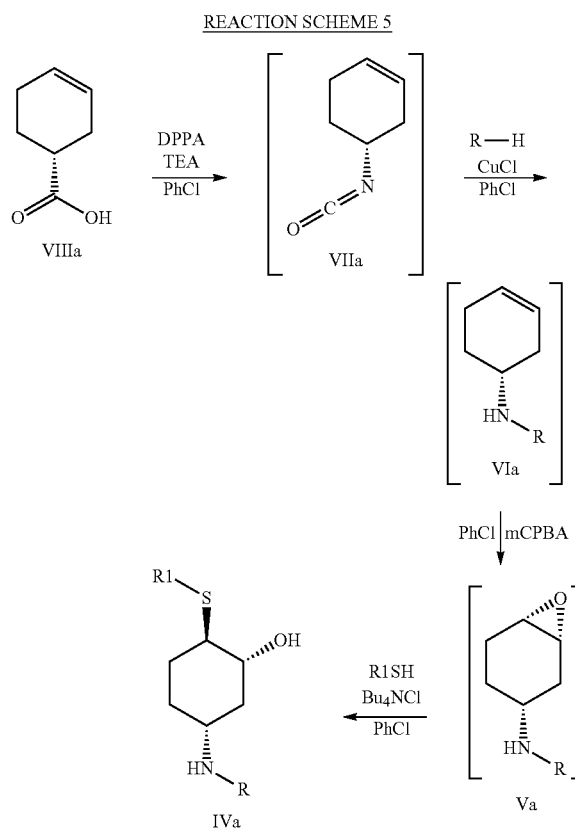

wherein R represents an amino protecting group and $R_1$ represents a sulfur protecting group and are defined as above.

Example 19

{(1R,2R,4R)-4-[(2,2,2-Trifluoroacetyl)-amino]-2-hydroxy-cyclohexyl}-benzene-carbothioate

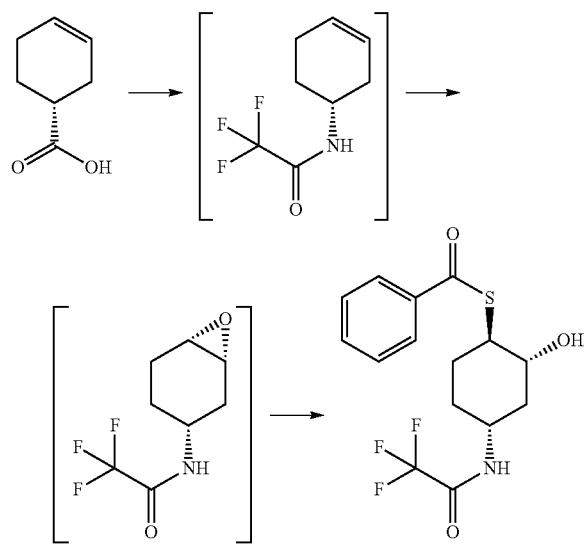

Step A: N-(Cyclohex-3-en-1(R)-yl)-2,2,2-trifluoro-acetamide 50 g of 3-cyclohexene-1(R)-carboxylic acid and 425 ml of chlorobenzene were charged to a flask at 20-25° C. and the mixture obtained was stirred. To the mixture obtained 110 ml of triethylamine was added dropwise followed by 25 ml of chlorobenzene. The mixture obtained was warmed to 78 to 82° C. and 109.2 g of DPPA was added in a dose controlled fashion, maintaining the temperature at 80 to 90° C. and steady gas evolution and a 20 ml of chlorobenzene line rinse was given. The mixture obtained was stirred at 78 to 82° C. for 1 h until complete determined by TLC. The mixture obtained was cooled to approximately 70° C. and 226 g of trifluoroacetic acid in 34 ml of chlorobenzene was added dropwise maintaining the temperature at 70 to 80° C., followed by 1.57 g of CuCl and a 25 ml chlorobenzene line rinse. The mixture obtained was stirred at 90 to 95° C. for 2 h and the reaction was followed by TLC until completion. The mixture obtained was cooled to 15 to 25° C. and 375 ml of 20% aqueous $K_2CO_3$ solution added and the mixture obtained was stirred for 15 min. The layers obtained were separated and to the upper organic layer obtained was added 375 ml of 20% aqueous $K_2CO_3$ solution. The mixture obtained was filtered through celite to remove residual solid and the celite was washed with 50 ml of chlorobenzene. The layers obtained were separated. The combined lower aqueous layers obtained were back extracted with 250 ml of chlorobenzene and the combined organic phases obtained were washed with 500 ml of 0.5 M phosphoric acid. The aqueous layer obtained was back extracted with 300 ml of chlorobenzene and the combined organic phases obtained were washed with 500 ml of 5% aqueous NaCl solution.

A strip weight assay was carried out to determine the N-(cyclohex-3-en-1(R)-yl)-2,2,2-trifluoro-acetamide content for use in epoxidation step B below.

The chlorobenzene solution obtained contained 69.52 g of N-(cyclohex-3-en-1(R)-yl)-2,2,2-trifluoro-acetamide.

$^1$H NMR (200 MHz, $D_6$-DMSO, ppm) δ 9.33 (d, 1H), 5.69-5.56 (m, 2H), 3.82 (s, broad, 1H), 2.25-1.96 (m, 4H), 1.81-1.74 (m, 1H), 1.66-1.58 (m, 1H)

MS (ESI, g/mol): m/z 194 [M+H]$^+$

Step B: 2,2,2-Trifluoro-N-(1R,3R,6S)-(7-oxa-bicyclo[4.1.0]hept-3-yl)-acetamide 106.5 g of m-Chloroperbenzoic acid (70%) was charged portionwise to the vessel containing the cooled (10-15° C.) solution of 69.5 g of the N-(cyclohex-3-en-1(R)-yl)-2,2,2-trifluoro-acetamide of step A maintaining temperature <30° C., and rinsed through with 69.5 ml of chlorobenzene. The mixture obtained was stirred at 20 to 25° C. for 1 h and the reaction was followed by TLC until completion. Upon completion of the reaction, the mixture obtained was cooled to 0 to −5° C., stirred for 30 min and the solid precipitate (mCBA) obtained was filtered off and washed with 2×34.8 ml of chlorobenzene. The resultant filtrate was washed with 347.6 ml of 10% sodium thiosulfate solution to remove peroxides, and the resultant aqueous layer was back extracted with 208.6 ml of chlorobenzene. The combined organic layers obtained were washed with 347.6 ml of 5% sodium bicarbonate solution to ensure a pH>7 of the aqueous phase and the resultant aqueous layer was back extracted with 208.6 ml of chlorobenzene. The combined organic layers were washed with 347.6 ml of water.

A strip weight assay was carried out to determine the 2,2,2-trifluoro-N-(1R,3R,6S)-(7-oxa-bicyclo[4.1.0]hept-3-yl)-acetamide content.

The chlorobenzene solution obtained contained 58.64 g of 2,2,2-trifluoro-N-(1R,3R,6S)-(7-oxa-bicyclo[4.1.0]hept-3-yl)-acetamide containing approximately 11% of anti (trans) epoxide and the organic solution was used for step C below (ring-opening).

$^1$H NMR (400 MHz, D$_6$-DMSO, ppm) δ 9.21 (d, J=7.2 Hz, 1H), 3.80-3.52 (m, 1H), 3.10-3.09 (m, 2H), 2.22-1.66 (m, 4H), 2.03-2.10 (m, 1H), 1.91-1.78 (m, 1H), 1.76-1.68 (m, 1H), 1.52-1.30 (m, 2H)

MS (ESI, g/mol): m/z 208 [MH]$^-$

Step C: {(1R,2R,4R)-4-[(2,2,2-Trifluoro-acetyl)-amino]-2-hydroxy-cyclohexyl}-benzene-carbothioate The chlorobenzene solution from step B containing 58.64 g of 2,2,2-trifluoro-N-(1R,3R,6S)-(7-oxa-bicyclo[4.1.0]hept-3-yl)-acetamide was concentrated to approximately 5 volumes based upon epoxide. The concentrate obtained was degassed at 15-25° C. with argon for 30 min and the temperature was adjusted to 15 to 20° C. To the mixture obtained 58.1 g of thiobenzoic acid (90%) was added dropwise ensuring a temperature below 30° C. To the mixture obtained 17.6 ml of chlorobenzene was added to the vessel as a line rinse and 2.49 g of tetrabutylammonium chloride monohydrate was added in portions at <30° C. The mixture obtained was heated to 40-45° C., stirred and the reaction followed by TLC until completion. Upon completion of the reaction, the mixture obtained was cooled to 0 to 5° C., stirred for 1 h and filtered, and the filter cake obtained was washed with 2×58.64 ml of chlorobenzene. The solid obtained was dried in vacuo at <40° C. 45.5 g of {(1R,2R,4R)-4-[(2,2,2-Trifluoro-acetyl)-amino]-2-hydroxy-cyclohexyl}-benzene-carbothioate was obtained in the form of a solid.

$^1$H NMR (400 MHz, DMSO-d$_6$, ppm) δ 9.38 (s, 1H), 7.91 (m, 2H), 7.68 (m, 1H), 7.55 (m, 2H), 5.23 (s, 1H), 3.80 (m, 1H), 3.55-3.49 (m, 1H), 3.41-3.34 (m, 1H), 2.13-2.03 (m, 2H), 1.82-1.79 (m, 1H), 1.60-1.38 (m, 3H).

MS (ESI, g/mol): m/z 348.0 [M+H]$^+$

The process to the starting material of the mixture of compound of formula IVa with a compound of formula IVb useful for the production of the mixture of compound of formula IIIa with a compound of formula IIIb is summarized in REACTION SCHEME 6 below:

REACTION SCHEME 6

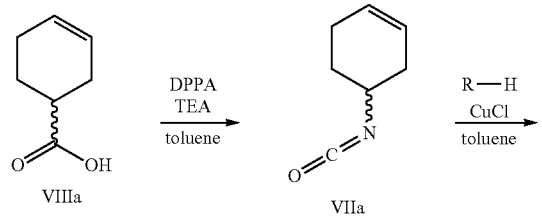

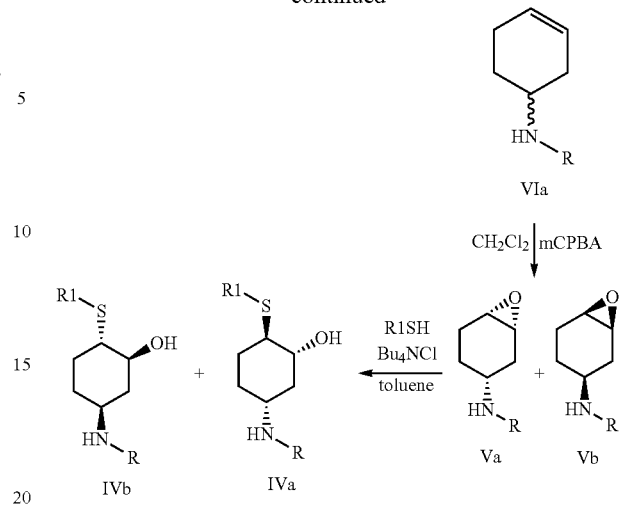

wherein R represents an amino protecting group and R1 represents a sulfur protecting group and are as defined above.

Example 20

{(1R,2R,4R)-4-[(tert-Butoxycarbonyl)-amino]-2-hydroxy-cyclohexyl}-benzene-carbothioate and {(1S,2S,4S)-4-[(tert-Butoxycarbonyl)-amino]-2-hydroxy-cyclohexyl}-benzene-carbothioate Step A: tert-Butyl cyclohex-3-enyl-1(R)-carbamate and tert-Butyl cyclohex-3-enyl-1(S)-carbamate

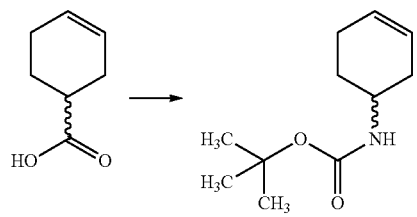

50.0 g of 3-cyclohexene-1-carboxylic acid and 500 ml of toluene were charged to a 2 L flask at 20-25° C., the mixture obtained was stirred and 60.7 ml of triethylamine was added dropwise over 15 min followed by dropwise addition of 89.7 ml of DPPA over 20 min (gas evolution, exotherm to ~50° C.). To the mixture obtained 50 ml of toluene was added as a line rinse. The mixture obtained was heated to reflux and stirred until the reaction was complete determined by TLC and $^1$H NMR. The reaction was shown to be complete after 1 h. The mixture obtained was cooled to 80° C. and 186 ml of t-BuOH was added dropwise over 10 min, followed by 1.26 g of CuCl and the mixture obtained was heated to reflux. The reaction was followed by $^1$H NMR, and was shown to be complete after 1 h. The mixture obtained was cooled to 20 to 25° C. and 250 ml of saturated NaHCO$_3$ solution was added over 5 to 10 min. The mixture obtained was stirred for 30 min, filtered to remove residual solid and the solid was rinsed with 25 ml of toluene. The layers were separated and the aqueous layer was extracted with 2×150 ml of toluene. The organic layers were combined, washed with 150 ml of water and concentrated in vacuo. 79.8 g of a mixture of tert-butyl cyclohex-3-enyl-1(R)- carbamate and tert-butyl cyclohex-3-enyl-1(S)-carbamate was obtained in the form of a brown solid.

Optical Rotation: $[\alpha]_D$ (CHCl$_3$)=0°
Purification by Column Chromatography:

The crude mixture of tert-butyl cyclohex-3-enyl-1(R)-carbamate and tert-butyl cyclohex-3-enyl-1(S)-carbamate was subjected to purification by column chromatography (eluent: cyclohexane/EtOAc 9:1).

The required clean fractions were identified and combined. Concentration under vacuum gave the required product. 60.88 g of a mixture of tert-Butyl cyclohex-3-enyl-1(R)-carbamate with tert-Butyl cyclohex-3-enyl-1(S)-carbamate was obtained in the form of a white solid.

Optical Rotation: $[\alpha]_D$ (CHCl$_3$)=0°
$^1$H NMR (200 MHz, CDCl$_3$, ppm) δ 5.69-5.53 (m, 2H), 4.55 (s, broad, 1H), 3.76 (s, broad, 1H), 2.41-2.30 (m, 1H), 2.12-2.08 (m, 2H), 1.91-1.76 (m, 2H), 1.6-1.48 (m, 1H), 1.43 (s, 9H)

Step B: tert-Butyl(1R,3R,6S)-(7-oxa-bicyclo[4.1.0]hept-3-yl)-carbamate and tert-Butyl(1S,3S,6R)-(7-oxa-bicyclo[4.1.0]hept-3-yl)-carbamate

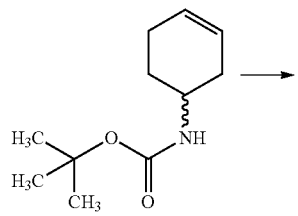

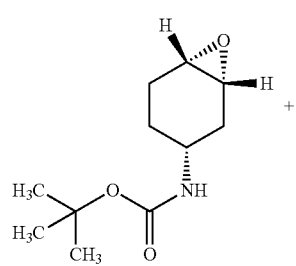

45 g of m-Chloroperbenzoic acid (70%) and 240 ml of CH$_2$Cl$_2$ were charged to a 1 L flask and the mixture obtained was cooled to 10 to 15° C. To the mixture obtained 30.0 g of tert-butyl cyclohex-3-enyl-1(R)-carbamate and tert-butyl cyclohex-3-enyl-1(S)-carbamate in 45 ml of CH$_2$Cl$_2$ was added dropwise over approximately 30 min ensuring a temperature below 25° C. To the mixture obtained 15 ml of CH$_2$Cl$_2$ was added as a line rinse and the mixture obtained was stirred at rt for 1 h, heated to reflux (40° C.) for 2 h and followed by HPLC and TLC until completion of the reaction. Upon completion of the reaction, the mixture obtained was cooled to 0 to 5° C., stirred for 30 min, and the solid precipitate (mCBA) obtained was filtered off and washed through with 2×15 ml of CH$_2$Cl$_2$. The resultant filtrate was washed with 3×150 ml of 10% aqueous sodium thiosulfate solution to remove peroxides, followed by 3×150 ml of saturated sodium bicarbonate solution to ensure a pH>7 (recorded pH=8-9), followed by 2×150 ml of water. The organic layer obtained was concentrated, 150 ml of toluene was added and the mixture obtained was concentrated again. To the concentrate obtained 150 ml of toluene was added, the mixture obtained was concentrated to dryness, toluene was added to approximately 2 volumes and the mixture obtained was kept in a refrigerator before use in the next step.

25.73 g of a mixture of tert-butyl(1R,3R,6S)-(7-oxa-bicyclo[4.1.0]hept-3-yl)-carbamate and tert-butyl(1S,3S,6R)-(7-oxa-bicyclo[4.1.0]hept-3-yl)-carbamate were obtained (the entire batch was evaporated to dryness, weighed and the contents of epoxide, mCBA and toluene were determined by NMR analysis). The material still contained mCBA and toluene.

The syn:anti ratio is 100:0 determined by $^1$H NMR.

Optical Rotation: $[\alpha]_D$ (CHCl$_3$)=0°
$^1$H NMR (200 MHz, CDCl$_3$, ppm) δ δ 4.82 (s, broad, 1H), 3.63-3.54 (m, 1H), 3.13 (s, 2H) 2.26-2.03 (m, 2H), 1.96-1.70 (m, 2H), 1.49-1.28 (m, 11H)

Step C: {(1R,2R,4R)-4-[tert-Butoxycarbonyl)-amino]-2-hydroxy-cyclohexyl}-benzene-carbothioate and {(1S,2S,4S)-4-[tert-Butoxycarbonyl)-amino]-2-hydroxy-cyclohexyl}-benzene-carbothioate

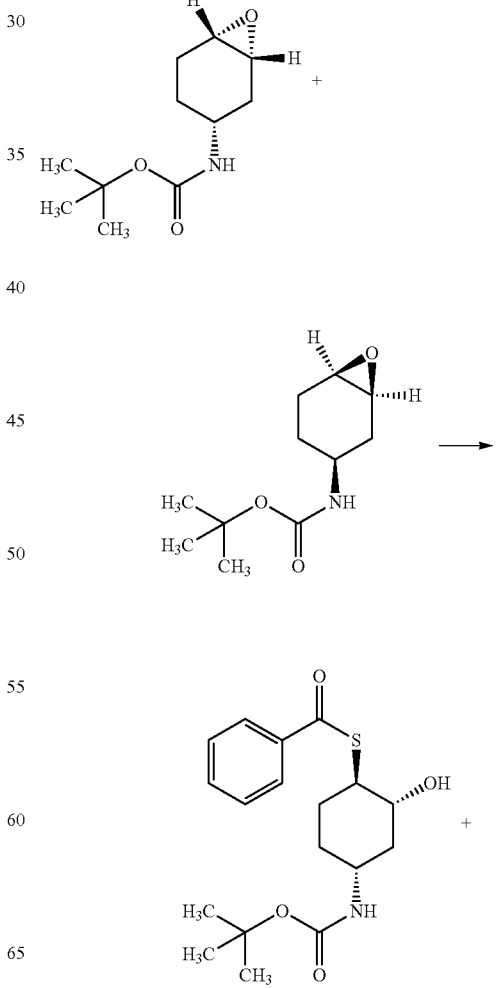

-continued

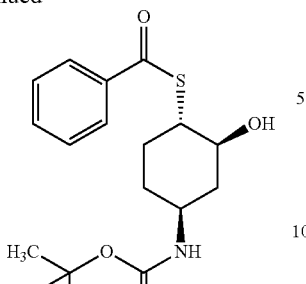

The product solution obtained in Step B containing 20.1 g of tert-Butyl(1R,3R,6S)-(7-oxa-bicyclo[4.1.0]hept-3-yl)-carbamate and tert-Butyl(1S,3S,6R)-(7-oxa-bicyclo[4.1.0]hept-3-yl)-carbamate and 60 ml of toluene were charged to a flask, the mixture obtained was stirred at 15-25° C. and 15 ml of thiobenzoic acid were melted and charged dropwise to the mixture obtained ensuring a temperature below 30° C. To the mixture obtained 18 ml of toluene was charged as a line rinse, 0.8 g of tetrabutylammonium chloride monohydrate was added in one portion, external temperature control was stopped and the mixture obtained was allowed to exotherm. The mixture obtained was heated to 40-45° C. and the reaction was followed by TLC until completion. Upon completion of the reaction (3 h), the mixture obtained was cooled to rt and washed twice with 2×101 ml of 5% sodium bicarbonate solution followed by 2×101 ml of water. The organic layer obtained was concentrated in vacuo to minimum volume. 101 ml of toluene was then charged and the batch again concentrated to minimum volume. This process was repeated and further 101 ml of toluene was added to the mixture obtained and the mixture was concentrated to ~40 ml. Water content was analyzed by KF (0.04%). To the mixture obtained 101 ml of toluene was added and the mixture obtained was concentrated to dryness.

Yield of crude material: 35.29 g.

To the crude material obtained was added 17.6 ml of toluene and the mixture obtained was cooled to 10 to 15° C. with stirring, at which point a solid precipitated. The slurry obtained was stirred for 45 min. To the mixture obtained 17.6 ml of heptane was added dropwise and the mixture obtained was stirred for 1 h. The mixture obtained was filtered, the solid obtained was allowed to pull dry and given a displacement wash with toluene-heptane (1:1, 8.8 ml), followed by a slurry wash with toluene-heptane (1:1, 17.6 ml) which reduced the amount of the undesired regioisomer to undetectable by NMR analysis. The solid obtained was dried in vacuo at ≤40° C. 8.24 g of a mixture of {(1R,2R,4R)-4-[tert-Butoxycarbonyl)-amino]-2-hydroxy-cyclohexyl}-benzene-carbothioate with {(1S,2S,4S)-4-[tert-Butoxycarbonyl)-amino]-2-hydroxy-cyclohexyl}-benzene-carbothioate was obtained in the form of an off-white solid.

Optical Rotation: $[\alpha]_D$ (CHCl$_3$)=0°

$^1$H NMR (200 MHz, DMSO-d$_6$, ppm) δ 7.91-7.87 (m, 2H), 7.70-7.50 (m, 3H), 6.85 (d, J=6 Hz, 1H), 5.13 (d, J=5.6 Hz, 1H), 3.50-3.26 (m, 3H), 2.13-1.96 (m, 2H), 1.79-1.69 (m, 1H), 1.54-1.15 (m, 12H)

The invention claimed is:

1. A compound of formula I

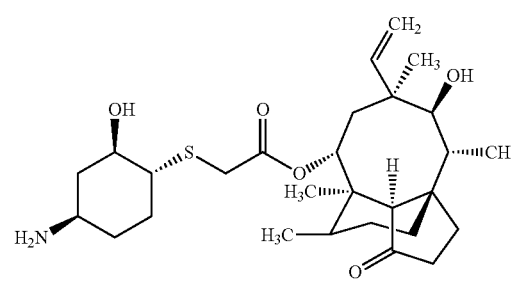

in the form of a single stereoisomer in crystalline form selected from the group consisting of:

crystalline Form 1, which is characterized by an X-ray powder diffraction pattern having at least two peaks 2-theta at (degrees, ±0.2): 10.6, 11.1, 12.0, 14.3, 15.1, 16.1, or 21.1;

crystalline Form 2, which is an n-butanol solvate characterized by an X-ray powder diffraction pattern having at least two peaks 2-theta at (degrees, ±0.2): 9.8, 11.1, 13.1, 14.1, 17.6, 19.7, or 22.2;

an acetate in crystalline Form A, which is characterized by an X-ray powder diffraction pattern having at least four peaks 2-theta at (degrees, ±0.2): 7.0, 7.7, 11.6, 12.1, 12.6, 13.5, 13.7, 15.4, 15.7, 16.9, 17.3, 19.0, 19.9, 21.1, 23.4, 24.2, or 24.4;

an acetate in crystalline Form B, which is characterized by an X-ray powder diffraction pattern having at least four peaks 2-theta at (degrees, ±0.2): 10.3, 10.7, 12.7, 14.3, 15.5, 16.0, 17.2, 19.5, 20.6, or 22.9;

an L-lactate in crystalline Form 1, which is characterized by an X-ray powder diffraction pattern having at least two peaks 2-theta at (degrees, ±0.2): 7.0, 11.6, 12.0, 12.5, 13.4, 13.6, 13.9, 15.3, 16.8, 18.8, 19.5, 19.8, 20.9, 23.3, 23.9, or 24.2; and a hydrogenmaleate in crystalline Form 1, which is characterized by an X-ray powder diffraction pattern having at least two peaks 2-theta at (degrees, ±0.2): 7.0, 11.3, 11.7, 12.5, 13.5, 13.8, 15.3, 16.7, 18.3, 19.4, 19.7, 21.1, 22.2, 23.8, or 23.9.

2. A compound according to claim 1, which is in crystalline Form 1.

3. A compound according to claim 2, in which the compound in crystalline Form 1 is characterized by an X-ray powder diffraction pattern having peaks 2-theta at (degrees, ±0.2): 10.6, 11.1, 12.0, 14.3, 15.1, 16.1, and 21.1.

4. A compound according to claim 1, which is in crystalline Form 2.

5. A compound according to claim 4, in which the compound in crystalline Form 2 is characterized by an X-ray powder diffraction pattern having peaks 2-theta at (degrees, ±0.2): 9.8, 11.1, 13.1, 14.1, 17.6, 19.7, and 22.2.

6. A compound according to claim 1, which is in the form of a crystalline salt.

7. A compound according to claim 6, wherein the crystalline salt is an acetate, lactate or hydrogenmaleate.

8. A compound according to claim 1, which is an acetate in crystalline Form A.

9. A compound according to claim 8, in which the acetate in crystalline Form A is characterized by an X-ray powder diffraction pattern having peaks 2-theta at (degrees, ±0.2): 7.0, 7.7, 11.6, 12.1, 12.6, 13.5, 13.7, 15.4, 15.7, 16.9, 17.3, 19.0, 19.9, 21.1, 23.4, 24.2, and 24.4.

10. A compound according to claim 1, which is an acetate in crystalline Form B.

11. A compound according to claim 10, in which the acetate in crystalline Form B is characterized by an X-ray powder diffraction pattern having peaks 2-theta at (degrees, ±0.2): 10.3, 10.7, 12.7, 14.3, 15.5, 16.0, 17.2, 19.5, 20.6, or 22.9.

12. A compound according to claim 1, which is an L-lactate in crystalline Form 1.

13. A compound according to claim 12, in which the L-lactate in crystalline Form 1 is characterized by an X-ray powder diffraction pattern having peaks 2-theta at (degrees, ±0.2): 7.0, 11.6, 12.0, 12.5, 13.4, 13.6, 13.9, 15.3, 16.8, 18.8, 19.5, 19.8, 20.9, 23.3, 23.9, and 24.2.

14. A compound according to claim 1, which is a hydrogenmaleate in crystalline Form 1.

15. A compound according to claim 14, in which the hydrogenmaleate in crystalline Form 1 is characterized by an X-ray powder diffraction pattern having peaks 2-theta at (degrees, ±0.2): 7.0, 11.3, 11.7, 12.5, 13.5, 13.8, 15.3, 16.7, 18.3, 19.4, 19.7, 21.1, 22.2, 23.8, or 23.9.

16. A pharmaceutical composition comprising the compound according to claim 1 as an active ingredient in combination with a pharmaceutically acceptable carrier or diluent.

17. A pharmaceutical composition comprising the compound according to any one of claim 2, 8, 10, 12, or 14 as an active ingredient in combination with a pharmaceutically acceptable carrier or diluent.

18. A process for the preparation of the compound of formula I according to claim 1, comprising deprotecting the amine group either in a compound of formula IIa

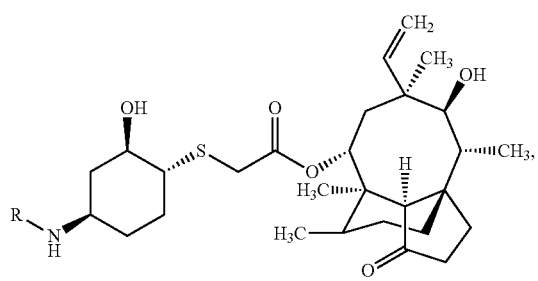

or in a mixture of a compound of formula IIa with a compound of formula IIb

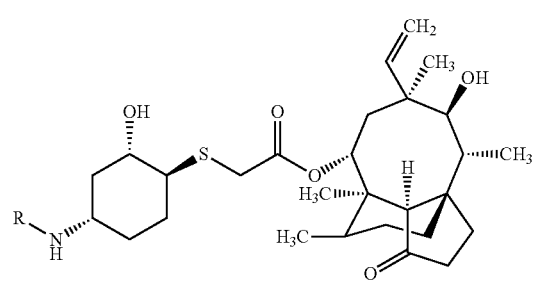

wherein R is an amine protecting group, and isolating a compound of formula I obtained in the form of a single diastereomer in crystalline form either directly from the reaction mixture or via recrystallization in organic solvent.

19. A process according to claim 1, wherein R in the compound of formula IIa is tert-butoxycarbonyl or trifluoroacetyl.

20. A pharmaceutical composition comprising the compound according to any one of claims 3 to 15 as an active ingredient in combination with a pharmaceutically acceptable carrier or diluent.

* * * * *

UNITED STATES PATENT AND TRADEMARK OFFICE
CERTIFICATE OF CORRECTION

| | | |
|---|---|---|
| PATENT NO. | : 9,120,727 B2 | Page 1 of 1 |
| APPLICATION NO. | : 13/699589 | |
| DATED | : September 1, 2015 | |
| INVENTOR(S) | : Riedl et al. | |

It is certified that error appears in the above-identified patent and that said Letters Patent is hereby corrected as shown below:

In the Specification

Column 3
Line 59, change "formula IIa" to --formula IIb--

Column 13
Line 31, change "mixture of compound" to --mixture of a compound--

Column 15
Line 36, change "proofen" to --proven--

Signed and Sealed this
Third Day of May, 2016

Michelle K. Lee
*Director of the United States Patent and Trademark Office*